US011272990B2

(12) United States Patent
Gudalo

(10) Patent No.: US 11,272,990 B2
(45) Date of Patent: Mar. 15, 2022

(54) SYSTEM AND METHOD OF UTILIZING THREE-DIMENSIONAL OVERLAYS WITH MEDICAL PROCEDURES

(71) Applicant: Alcon Inc., Fribourg (CH)

(72) Inventor: Aleksander Gudalo, Berlin (DE)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/078,026

(22) Filed: Oct. 22, 2020

(65) Prior Publication Data

US 2021/0121246 A1 Apr. 29, 2021

Related U.S. Application Data

(60) Provisional application No. 62/927,413, filed on Oct. 29, 2019.

(51) Int. Cl.
*A61B 34/00* (2016.01)
*A61B 5/00* (2006.01)
(Continued)

(52) U.S. Cl.
CPC ............ *A61B 34/25* (2016.02); *A61B 5/7445* (2013.01); *A61B 90/20* (2016.02);
(Continued)

(58) Field of Classification Search
CPC ........ A61B 2090/364; A61B 2090/035; A61B 2090/3983; A61B 3/13; A61B 90/39; A61B 34/25; A61B 3/0025; A61B 3/0058; A61B 3/1216; A61B 3/132; A61B 3/14; A61B 5/7445; A61B 90/20; G02B 2027/0138; G02B 2027/014; G02B 2027/0141; G02B 27/0101; G06T 19/006; G06T 11/60;
(Continued)

(56) References Cited

U.S. PATENT DOCUMENTS

2005/0117118 A1  6/2005  Miller
2010/0094262 A1* 4/2010  Tripathi ............... A61B 3/0033
                                                   606/1
(Continued)

FOREIGN PATENT DOCUMENTS

WO         0128476 A1    4/2001

*Primary Examiner* — Jin Cheng Wang

(57) ABSTRACT

The disclosure provides a system that may: render, based at least on first positions of locations of iris structures of an eye, a first two-dimensional overlay image associated with a three-dimensional image overlay image; display, via a first display, the first two-dimensional overlay image; render, based at least on the first positions and at least on a horizontal offset, a second two-dimensional overlay image associated with the three-dimensional overlay image; display, via a second display, the second two-dimensional overlay image; render, based at least on second positions, a third two-dimensional overlay image associated with the three-dimensional overlay image; display, via the first display, the third two-dimensional overlay image; render, based at least on second positions of locations of the iris structures and at least on the horizontal offset, a fourth two-dimensional overlay image associated with the three-dimensional overlay image; and display, via the second display, the fourth two-dimensional overlay image.

14 Claims, 18 Drawing Sheets

(51) Int. Cl.
| | |
|---|---|
| *A61B 90/20* | (2016.01) |
| *G02B 27/01* | (2006.01) |
| *G06F 3/14* | (2006.01) |
| *G06T 19/00* | (2011.01) |
| *G06T 7/00* | (2017.01) |
| *G06T 7/70* | (2017.01) |
| *G06K 9/00* | (2022.01) |

(52) U.S. Cl.
CPC ....... *G02B 27/0101* (2013.01); *G06F 3/1423* (2013.01); *G06T 7/0004* (2013.01); *G06T 7/70* (2017.01); *G06T 19/006* (2013.01); *G02B 2027/014* (2013.01); *G02B 2027/0138* (2013.01); *G02B 2027/0141* (2013.01); *G06K 9/00604* (2013.01); *G06T 2207/10056* (2013.01); *G06T 2207/30041* (2013.01); *G06T 2210/41* (2013.01)

(58) Field of Classification Search
CPC . G06T 2207/10028; G06T 2207/10056; G06T 2207/30041; G06T 2210/41; G06T 7/0004; G06T 7/70; G06T 7/73; G06K 9/00604; G06K 9/0061
See application file for complete search history.

(56) References Cited

U.S. PATENT DOCUMENTS

| | | | |
|---|---|---|---|
| 2010/0217278 A1* | 8/2010 | Tripathi | A61F 2/16 606/130 |
| 2018/0360310 A1* | 12/2018 | Berlin | A61B 3/13 |
| 2019/0117459 A1* | 4/2019 | Berlin | A61B 3/102 |
| 2019/0151024 A1* | 5/2019 | Abraham | A61B 90/39 |
| 2020/0292307 A1* | 9/2020 | Seitz | G01B 11/002 |

* cited by examiner

SYSTEM AND METHOD OF UTILIZING THREE-DIMENSIONAL OVERLAYS WITH MEDICAL PROCEDURES

BACKGROUND

Field of the Disclosure

This disclosure relates to utilizing three-dimensional overlays and more particularly to utilizing three-dimensional overlays with medical procedures.

Description of the Related Art

In the past, limited information was provided to a surgeon during a surgery. For example, the surgeon may operate on a portion of a patient in three-dimensions. The portion of the patient may include an eye of the patient. For example, the eye of the patient is three-dimensional. Providing information to the surgeon using flat images did not take into account depth that is associated with three-dimensions. Accordingly, graphics may not accurately indicate one or more positions on a three-dimensional portion of the patient. In one example, graphics may not accurately indicate one or more positions on the eye of the patient. In another example, the graphics may not accurately indicate one or more incision locations on the eye of the patient.

SUMMARY

The present disclosure provides a system able to receive a first image of an eye of a patient. For example, the first image of the eye of the patient may be received from a camera. The system may further determine locations of multiple iris structures of the eye of the patient from the first image of the eye of the patient. The system may further determine first positions of the locations of the multiple iris structures. The system may further render, based at least on the first positions of the locations of the multiple iris structures, a first two-dimensional overlay image associated with a three-dimensional overlay image. For example, the three-dimensional overlay image may include at least one graphic that indicates an incision location associated with the eye of the patient. The system may further display, via a first display of the system, the first two-dimensional overlay image associated with the three-dimensional overlay image. The system may further render, based at least on the first positions of the locations of the multiple iris structures and based at least on a horizontal offset, a second two-dimensional overlay image associated with the three-dimensional overlay image. The system may further display, via a second display of the system, the second two-dimensional overlay image associated with the three-dimensional overlay image. The system may further receive a second image of the eye of the patient. The system may further determine second positions of the locations of the multiple iris structures from the second image of the eye of the patient. The system may further render, based at least on the second positions of the locations of the multiple iris structures, a third two-dimensional overlay image associated with the three-dimensional overlay image. The system may further display, via the first display, the third two-dimensional overlay image associated with the three-dimensional overlay image. The system may further render, based at least on the second positions of the locations of the multiple iris structures and based at least on the horizontal offset, a fourth two-dimensional overlay image associated with the three-dimensional overlay image. The system may further display, via the second display, the fourth two-dimensional overlay image associated with the three-dimensional overlay image.

The system may further determine that the locations of the multiple iris structures are not at the first positions. For example, determining the second positions of the locations of the multiple iris structures may be performed in response to determining that the locations of the multiple iris structures are not at the first positions.

The horizontal offset may be an interocular distance. The interocular distance may be associated with a distance between eyes of a surgeon. The system may include multiple eye pieces. The system may further determine a distance between two eye pieces of the multiple eye pieces. The system may further determine the interocular distance based at least on the distance between two eye pieces. The system may include a microscope integrated display. For example, the microscope integrated display may include the two eye pieces of the multiple eye pieces. Displaying, via the first display, the first two-dimensional overlay image associated with the three-dimensional overlay image may include displaying the first two-dimensional overlay image associated with the three-dimensional overlay image via a first eye piece of the two eye pieces. Displaying, via the second display, the second two-dimensional overlay image associated with the three-dimensional overlay image may include displaying the second two-dimensional overlay image associated with the three-dimensional overlay image via a second eye piece of the two eye pieces. Determining the first positions of the locations of the multiple iris structures may include determining at least one of a first angle associated with a X-axis, a second angle associated with a Y-axis, and an angle of rotation about an arbitrary axis.

The present disclosure further includes a non-transient computer-readable memory device with instructions that, when executed by a processor of a system, cause the system to perform the above steps. The present disclosure further includes a system or a non-transient computer-readable memory device as described above with one or more of the following features, which may be used in combination with one another unless clearly mutually exclusive: i) receive a first image of an eye of a patient; ii) determine locations of multiple iris structures of the eye of the patient from the first image of the eye of the patient; iii) determine first positions of the locations of the multiple iris structures; iv) render, based at least on the first positions of the locations of the multiple iris structures, a first two-dimensional overlay image associated with a three-dimensional overlay image; v) display, via a first display, the first two-dimensional overlay image associated with the three-dimensional overlay image; vi) render, based at least on the first positions of the locations of the multiple iris structures and based at least on a horizontal offset, a second two-dimensional overlay image associated with the three-dimensional overlay image; vii) display, via a second display, the second two-dimensional overlay image associated with the three-dimensional overlay image; viii) receive a second image of the eye of the patient; ix) determine second positions of the locations of the multiple iris structures from the second image of the eye of the patient; x) render, based at least on the second positions of the locations of the multiple iris structures, a third two-dimensional overlay image associated with the three-dimensional overlay image; xi) display, via the first display, the third two-dimensional overlay image associated with the three-dimensional overlay image; xii) render, based at least on the second positions of the locations of the multiple iris structures and based at least on the horizontal offset, a fourth two-dimensional overlay image associated with the three-dimensional overlay image; xiii) display, via the second display, the fourth two-dimensional overlay image associated with the three-dimensional overlay image; xix) determine that the locations of the multiple iris structures are not at the first positions; xx) determine a distance between two eye pieces of multiple eye pieces; and xxi) determine the interocular distance based at least on the distance between two eye pieces.

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

It is to be understood that both the foregoing general description and the following detailed description are examples and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which.

DETAILED DESCRIPTION

Figure 1A:
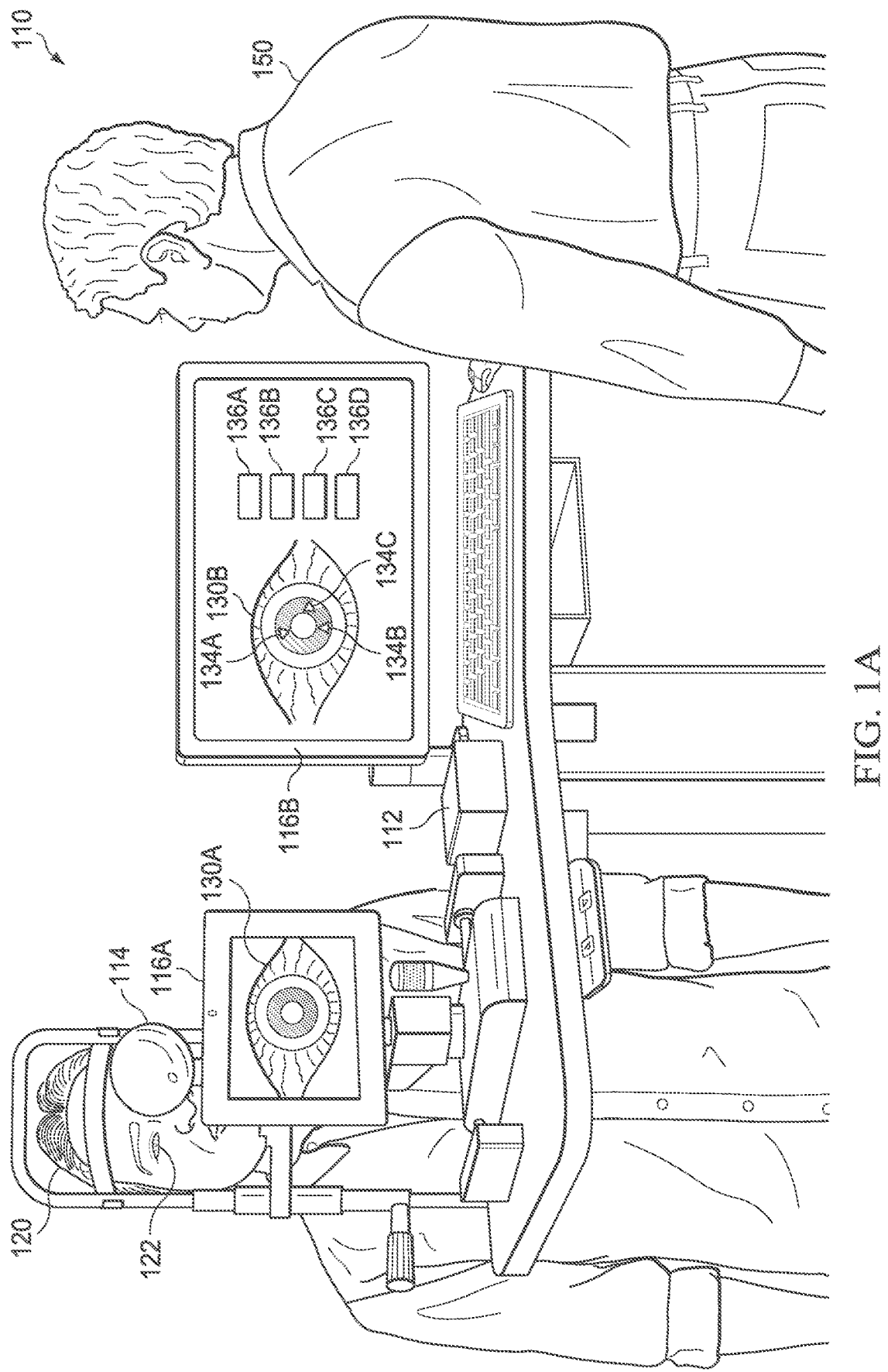
FIG. 1A illustrates an example of a medical system.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

Medical systems may be utilized in performing medical procedures with patients. In one example, a first medical system may be utilized, at a first time, in identifying one or more portions of a patient before a medical procedure. In a second example, a second medical system may be utilized, at a second time, in performing the medical procedure. In another example, the second medical system may utilize, at the second time, one or more identifications respectively associated with the one or more portions of the patient. The second time may be a later time than the first time. In one example, the first medical system may be utilized at an office of a doctor. In another example, the second medical system may be utilized at a surgical facility.

The first medical system may determine structures of an iris of an eye of the patient. For example, determining the structures of the iris of the eye of the patient may include identifying the structures of the iris of the eye of the patient. The second medical system may utilize the structures of the iris of the eye of the patient to display one or more three-dimensional overlays. For example, the one or more three-dimensional overlays may indicate information associated with the eye of the patient. The information associated with the eye of the patient may include one or more of positioning, an incision location, capsulorhexis, and centration, among others. In one example, the second medical system may be and/or may include an augmented reality system. In another example, the second medical system may provide an augmented reality via the one or more three-dimensional overlays. The second medical system may include a microscope. For example, the one or more three-dimensional overlays may be displayed via the microscope.

The second medical system may include a microscope integrated display (MID). The MID may provide one or more three-dimensional images to a surgeon. For example, the one or more three-dimensional images may include one or more three-dimensional overlay images. The MID may include multiple displays. The MID may provide the one or more three-dimensional images to the surgeon via the multiple displays. The MID may simulate one or more appearances of depth in providing the one or more three-dimensional images. The surgeon may perceive the one or more images as three-dimensional. For example, a first display of the MID may provide a two-dimensional overlay image to the surgeon, and a second display may concurrently provide a second two-dimensional overlay image to the surgeon. The second two-dimensional overlay image may be slightly different from the first two-dimensional overlay image. For example, a difference of the second two-dimensional overlay image from the first two-dimensional overlay image may be in a relative horizontal position of an object in the second two-dimensional overlay image and the first two-dimensional overlay image. A positional difference of the object in the first two-dimensional overlay image and the object in the second two-dimensional overlay image may be referred to as a horizontal disparity. More generally, for example, the positional difference of the object in the first two-dimensional overlay image and the object in the second two-dimensional overlay image may be referred to as a binocular disparity.

The displays may provide an illusion of depth from "flat" images (e.g., two-dimensional images) that differ in horizontal disparity. For example, the first display may provide the first two-dimensional overlay image to a left eye of the surgeon, and the second display may provide the second two-dimensional overlay image to a right eye of the surgeon. When the surgeon views the first two-dimensional overlay image with the left eye and concurrently views the second two-dimensional overlay image the right eye, the surgeon may see a single three-dimensional overlay image. For example, a brain of the surgeon may accept a small horizontal disparity between the first overlay image to the left eye of the surgeon and the second overlay image to the right eye of the surgeon, which may permit the surgeon to see (e.g., perceive) a single overlay image with depth. This may be referred to as stereoscopy. The single overlay image with depth may be a three-dimensional overlay image.

A stereo overlay image may be produced via creating the first two-dimensional overlay image and the second two-dimensional overlay image. For example, the first two-dimensional overlay image may be a flat first image, and the second two-dimensional overlay image may be a flat second image. The first flat first image and the second flat image may be referred to as a stereo pair. For example, the first flat first image may be for a left eye, and the second flat first image may be for a right eye. The first flat image may be rendered with respect to a position of the left eye. The second flat image may be rendered via applying a horizontal offset to the position of the left eye. For example, the horizontal offset may be an interocular distance. A typical interocular distance, for example, may be around 6.5 cm. Other interocular distances may be utilized.

The MID may determine an interocular distance. For example, eye pieces of the MID may be adjustable. The eye pieces of the MID may be adjusted for an interocular distance associated with the surgeon. A sensor of the MID may be utilized in determining a distance between the eye pieces of the MID. For example, an interocular distance associated with the surgeon may be determined based at least on the distance between the eye pieces of the MID.

When an eye of a patient moves, a three-dimensional overlay image displayed by the MID may move. For example, the three-dimensional overlay image displayed by the MID may move in accordance with one or more movements of the eye of the patient. Multiple iris structures of the eye of the patient may be tracked. For example, the three-dimensional overlay image displayed by the MID may move in accordance with one or more movements of the eye of the patient based at least on tracking the multiple iris structures of the eye of the patient.

The MID may display the three-dimensional image when the eye of the patient is in a first position. The eye of the patient may move to a second position. In one example, the eye may move left or right. In a second example, the eye may move up or down. In third example, the eye may rotate clockwise or counterclockwise. In another example, the eye may moved in a combination of left or right, up or down, and clockwise or counterclockwise. The MID may display the three-dimensional overlay image when the eye of the patient is in a second position. For example, the eye may be in the second position after the eyes moves. The first position of the eye and the second position of the eye may be determined via the multiple iris structures of the eye. The MID may display the three-dimensional overlay image when the eye of the patient is in the second position. For example, the three-dimensional overlay image may be displayed in relation to movements of the eye of the patient.

Turning now to FIG. 1A, an example of a medical system is illustrated. As shown, a medical system 110 may be utilized with a patient 120. As illustrated, medical system 110 may include a computer system 112. Computer system 112 may be communicatively coupled to displays 116A and 116B. Computer system 112 may be communicatively coupled to a biometry device 114. In one example, biometry device 114 may include one or more cameras. In another example, biometry device 114 may include a three-dimensional scanner. Biometry device 114 may be utilized in biometry of an eye 122 of patient 120. As shown, display 116A may display an image 130A associated with eye 122 of patient 120. As illustrated, display 116B may display an image 130B associated with eye 122 of patient 120.

Computer system 112 may determine eye recognition information. For example, the eye recognition information may include biometry information associated with eye 122 of patient 120. The biometry information associated with eye 122 may include one or more of a pattern of blood vessels of a sclera of eye 122, a structure of an iris of eye 122, a position of a structure of an iris of eye 122, a distance measurement of a cornea of eye 122 to a lens of eye 122, a distance measurement of a lens of eye 122 to a retina of eye 122, a corneal topography of eye 122, a retinal pattern of eye 122, and a wavefront measurement, among others.

As shown, display 116B may display structures of an iris 134A-134C of eye 122. As illustrated, display 116B may display display areas 136A-136D. In one example, a display area 136 may display a distance measurement of a cornea of eye 122 to a lens of eye 122, a distance measurement of a lens of eye 122 to a retina of eye 122, a position of a structure of an iris 134, corneal topography information, or wavefront measurement information, among other biometry information associated with eye 122. In another example, a display area 136 may display any information associated with patient 120.

A person 150 may operate medical system 110. For example, person 150 may be medical personnel. Person 150 may enter identification information associated with patient 120 into computer system 112. The identification information associated with patient 120 may include one or more of a name of patient 120, an address of patient 120, a telephone number of patient 120, a government issued identification number of patient 120, a government issued identification string of patient 120, and a date of birth of patient 120, among others.

Person 150 may provide medical procedure information, associated with patient 120, to computer system 112. The medical procedure information may be associated with a medical procedure. The medical procedure information may be associated identification information associate with patient 120. Computer system 112 may store the medical procedure information. For example, computer system 112 may store the medical procedure information for later utilization. The medical procedure information may be associated with a surgery. For example, the medical procedure information may be retrieved before the surgery. The medical procedure information may be utilized during a medical procedure. For example, the medical procedure may include a surgery.

Figure 1B:
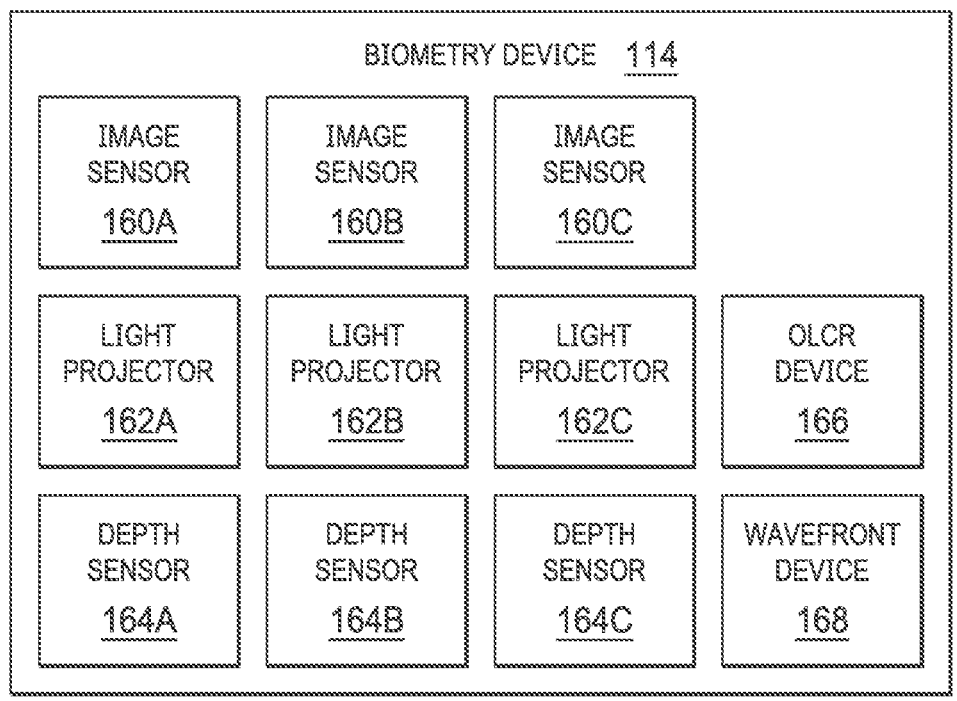
FIG. 1B illustrates an example of a biometry device.

Turning now to FIG. 1B, an example of a biometry device is illustrated. As shown, biometry device 114 may include image sensors 160A-160C. For example, an image sensor 160 may include a camera. A camera may include a one or more digital image sensors. In one example, a digital image sensor may include a charge-coupled device (CCD). In another example, a digital image sensor may include a complementary metal-oxide-semiconductor (CMOS). The camera may transform light into digital data. The camera may utilize a Bayer filter mosaic. For example, the camera may utilize a Bayer filter mosaic in combination with an optical anti-aliasing filter. A combination of the Bayer filter mosaic in combination with the optical anti-aliasing filter may reduce aliasing due to reduced sampling of different primary-color images. The camera may utilize a demosaicing process. For example, the demosaicing process may be utilized to interpolate color information to create a full array of red, green, and blue (RGB) image data.

As illustrated, biometry device 114 may include light projectors 162A-162C. In one example, a light projector 162 may project visible light. In another example, a light projector 162 may project infrared light. A light projector 162 may project circles and/or dots onto an eye of a patient. An image sensor 160 may receive reflections of the circles and/or the dots that were projected onto the eye of the patient. A computer system may determine one or more locations and/or one or more templates associated with the eye of the patient based at least on the reflections of the circles and/or the dots that were projected onto the eye of the patient. As shown, biometry device 114 may include depth sensors 164A-164C. A depth sensor 164 may include a light projector 162. A depth sensor 164 may include an optical sensor. As illustrated, biometry device 114 may include an optical low coherence reflectometer (OLCR) device 166. As shown, biometry device 114 may include a wavefront device 168.

Wavefront device 168 may include one or more of a light source and a wavefront sensor, among others. A light source may provide a first light wave to eye 122. A wavefront sensor may receive a first perturbed light wave, based at least on the first light wave, from eye 122. In one example, wavefront device 168 may determine first optical corrections based at least on the first perturbed light. In another example, a computer system may determine first optical corrections based at least on the first perturbed light. Wavefront device 168 may provide data, based at least on the first perturbed light wave, to a computer system. For example, the computer system may determine first optical corrections based at least on the data from wavefront device 168.

Any two or more of an image sensor 160, a light projector 162, a depth sensor 164, an OLCR device 166, and a wavefront device 168 may be combined. One or more of image sensors 160A-160C, one or more of light projectors 162A-162C, one or more of depth sensors 164A-164C, OLCR device 166, and/or wavefront device 168, among others, may produce data that may be utilized by a computer system.

Figure 2A:
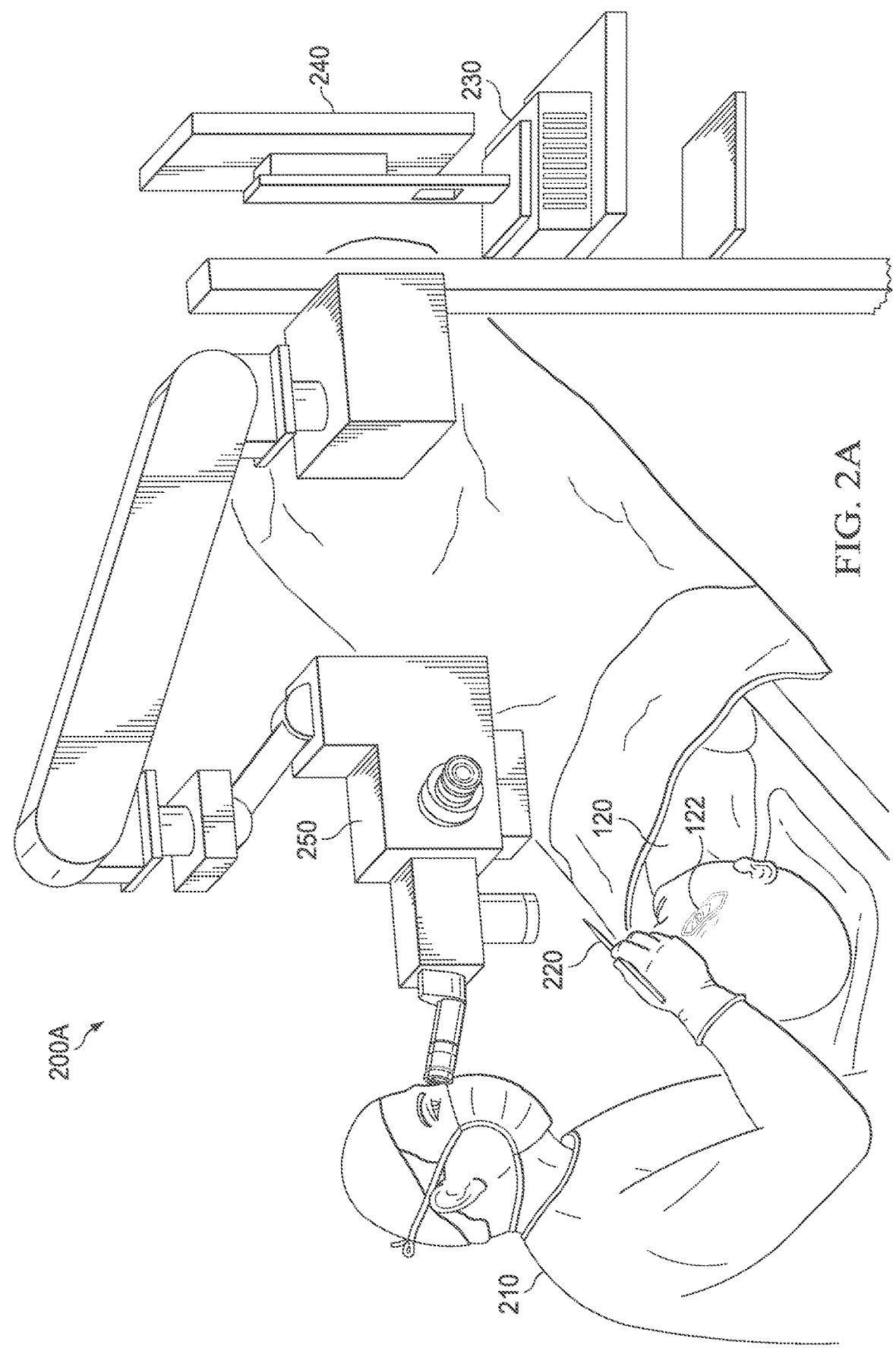
FIG. 2A illustrates a second example of a medical system.

Turning now to FIG. 2A, a second example of a medical system is illustrated. As shown, a surgeon 210 may utilize surgical tooling equipment 220. In one example, surgeon 210 may utilize surgical tooling equipment 220 in a surgery involving eye 122 of patient 120. A medical system 200A may include an ophthalmic surgical tool tracking system. As illustrated, medical system 200A may include a computer system 230, a display 240, and a MID 250.

Computer system 230 may receive image frames captured by one or more image sensors. For example, computer system 230 may perform various image processing on the one or more image frames. Computer system 230 may perform image analysis on the one or more image frames to identify and/or extract one or more images of surgical tooling equipment 220 from the one or more image frames. Computer system 230 may generate a graphical user interface (GUI), which may overlay the one or more image frames. For example, the GUI may include one or more indicators and/or one or more icons, among others. The one or more indicators may include surgical data, such as one or more positions and/or one or more orientations. The one or more indicators may include one or more warnings. The GUI may be displayed by display 240 and/or MID 250 to surgeon 210 and/or other medical personnel.

Computer system 230, display 240, and MID 250 may be implemented in separate housings communicatively coupled to one another or within a common console or housing. A user interface may be associated with one or more of computer system 230, display 240, and MID 250, among others. For example, a user interface may include one or more of a keyboard, a mouse, a joystick, a touchscreen, an eye tracking device, a speech recognition device, a gesture control module, dials, and/or buttons, among other input devices. A user (e.g., surgeon 210 and/or other medical personnel) may enter desired instructions and/or parameters via the user interface. For example, the user interface may be utilized in controlling one or more of computer system 230, display 240, and MID 250, among others.

Figure 2B:
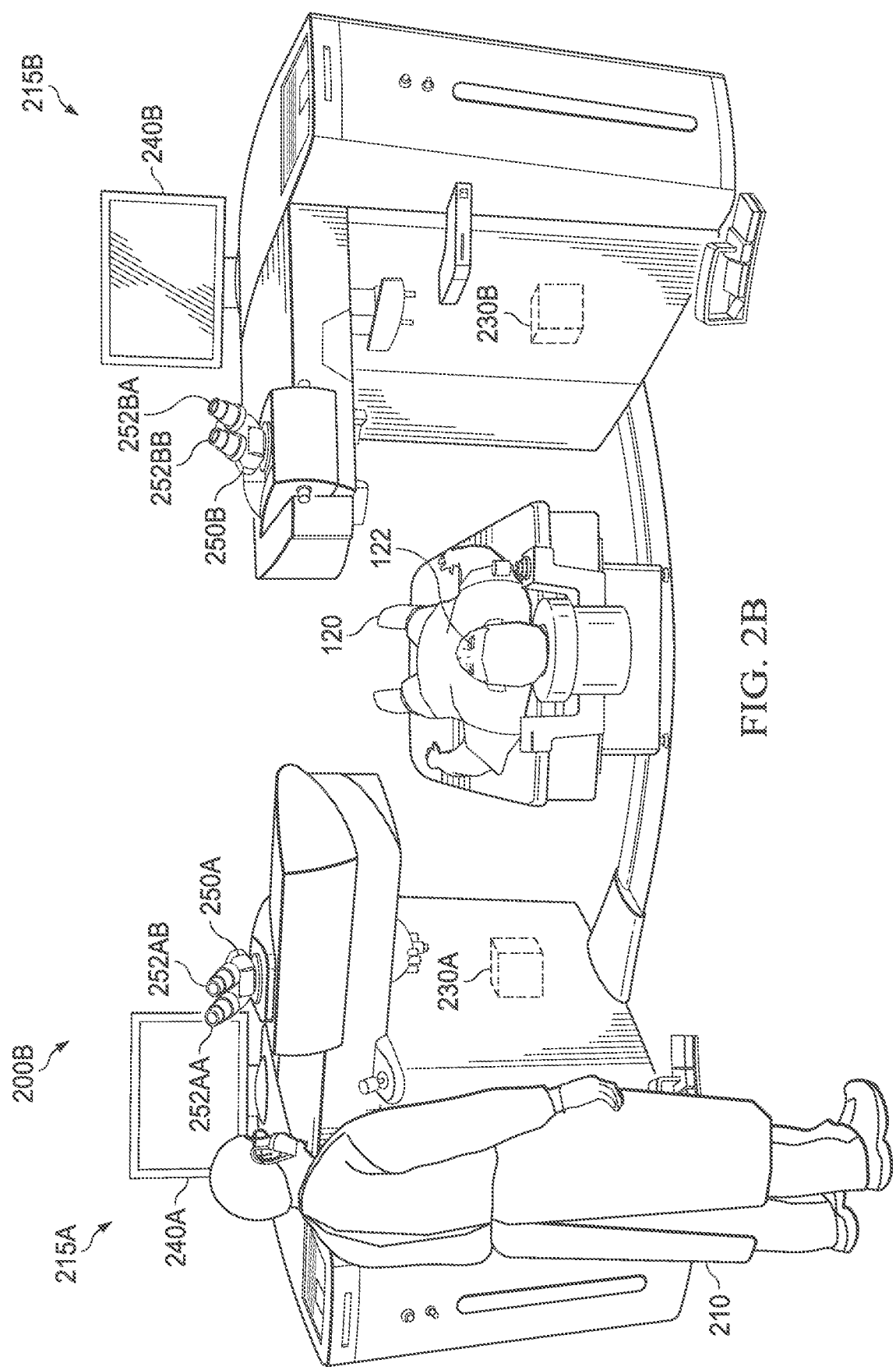
FIG. 2B illustrates another example of a medical system.

Turning now to FIG. 2B, another example of a medical system is illustrated. As shown, a surgeon 210 may utilize a system 200B. For example, surgeon 210 may utilize system 200B in a surgery involving eye 122 of patient 120. System 200B may include multiple systems. As shown, system 200B may include a cutting system 215A. For example, surgeon 210 may utilize system 215A in cutting eye 122. Eye 122 may include a flap in a cornea of an eye of patient 120. As illustrated, system 200B may include a shaping system 215B. For example, surgeon 210 may utilize shaping system 215B in performing ablation on an interior part of the cornea of eye 122.

As shown, system 215A may include a display 240A. As illustrated, system 215A may include a MID 250A. As illustrated, MID 250A may include eye pieces 252AA and 252AB. An eye piece 252A may refer to an eye piece 252AA or to an eye piece 252BA. An eye piece 252B may refer to an eye piece 252AB or to an eye piece 252BB. System 215A may include one or more of image sensors 160A-160C, one or more of light projectors 162A-162C, one or more of depth sensors 164A-164C, OLCR device 166, and/or wavefront device 168, among others. As illustrated, system 215B may include a display 240B. As shown, system 215B may include a MID 250B. As illustrated, MID 250B may include eye pieces 252BA and 252BB. System 215B may include one or more of image sensors 160A-160C, one or more of light projectors 162A-162C, one or more of depth sensors 164A-164C, OLCR device 166, and/or wavefront device 168, among others.

System 215A may include a laser, such as a femtosecond laser, which may use short laser pulses to ablate a series of small portions of corneal tissue to form a flap that may be lifted up to expose an interior part of the cornea. The flap may be planned and cut using one or both of cutting device displays 240A and 250A, along with control devices and a computer system 230A. As shown, system 215A may include computer system 230A. For example, computer system 230A may be coupled to one or more of image sensors 160A-160C, one or more of light projectors 162A-162C, one or more of depth sensors 164A-164C, OLCR device 166, and/or wavefront device 168, among others, of system 215A. As illustrated, system 215B may include computer system 230B. For example, computer system 230B may be coupled to one or more of image sensors 160A-160C, one or more of light projectors 162A-162C, one or more of depth sensors 164A-164C, OLCR device 166, and/or wavefront device 168, among others, of system 215B.

Systems 215A and 215B may be physically separated as shown in FIG. 2B. Patient 120 may be moved between systems 215A and 215B. Alternatively, patient 120 may remain stationary and systems 215A and 215B may be moved to patient 120. Systems 215A and 215B may be physically combined into a single unitary device, such that neither the device nor patient 120 is repositioned when switching between systems 215A and 215B.

System 200B may include one or more control devices for controlling systems 215A and 215B. For example, the one or more control devices may include one or more of an interactive display, such as a touchscreen display, a keyboard, a mouse, a touchpad, buttons, a joystick, a foot pedal, a heads-up display, and virtual-reality glasses, or other devices able to interact with a user, such as medical personnel.

System 200B may include at least one computer system configured to generate an image presented on at least one of displays 240A, 250A, 240B, and 250B, among others. For example, the at least one computer system may include one or more of computer systems 230A and 230B. One or more of computer systems 230A and 230B may be coupled to observational devices, such as a microscope, a camera, an optical coherence tomography (OCT) device or display, or another device able to measure the position of the eye undergoing surgery. One or more of computer systems 230A and 230B may be coupled to one or more of the control devices.

In one example, cutting device computer system 230A: i) may be coupled to observational devices that observe the eye when patient 120 is positioned with system 215A, ii) may provide graphical information regarding the planned flap location and the planned area of ablation to one or more of displays 240A and 250A, and iii) may be coupled to one or more control devices of system 215A. In a second example, shaping device computer 230B: i) may be coupled to observational devices that observe the eye when patient 120 is positioned with a shaping device, ii) may provide graphical information regarding the planned flap location and the planned area of ablation to one or more of displays 240B and 250B, and iii) may be coupled to one or more control devices of system 215B. In another example, a computer system may include the properties and/or the attributes described above with respect to one or more of computer systems 230A and 230B, among others.

A computer system of a system 200 may be coupled to another part of system 200 in a wired fashion or in a wireless fashion. One of more of computer systems of system 200 may be coupled to a database, stored locally, on a remote computer system or a remote data center, or both, that store patient data, treatments plans, and/or other information associated with medical treatments and/or system 200. In one example, the database may include a relational database. In a second example, the database may include a graph database. In another example, the database may include a "Not Only SQL" (NoSQL) database.

System 200 may enter information regarding patient 120 and the treatment to be performed on patient 120 or actually performed on patient 120. System 200 may allow a user to enter and view information regarding patient 120 and the treatment to be performed on patient 120. Such data may include information about patient 120, such as identifying information, a medical history of patient 120, and information about eye 122 being treated. Such data may include information about the treatment plans, such as the shape and location of a corneal cut and a shape and location of ablation, among others.

Figure 2C:
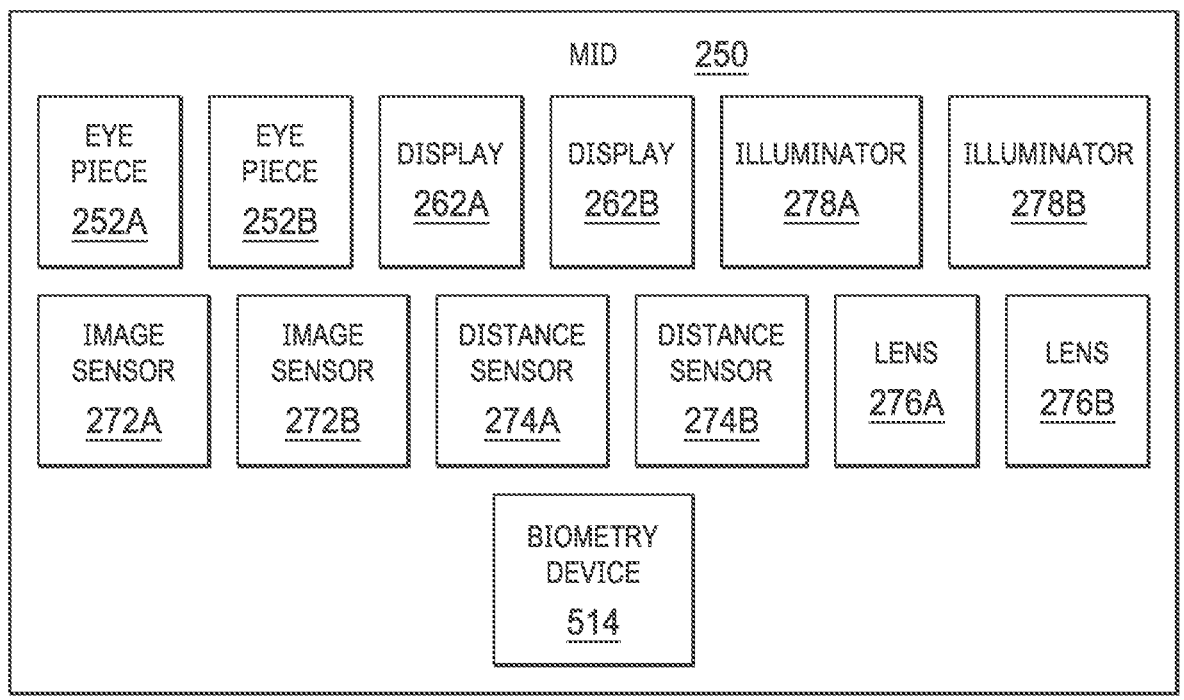
FIG. 2C illustrates an example of a microscope integrated display and examples of surgical tooling equipment.
Figure 2C:
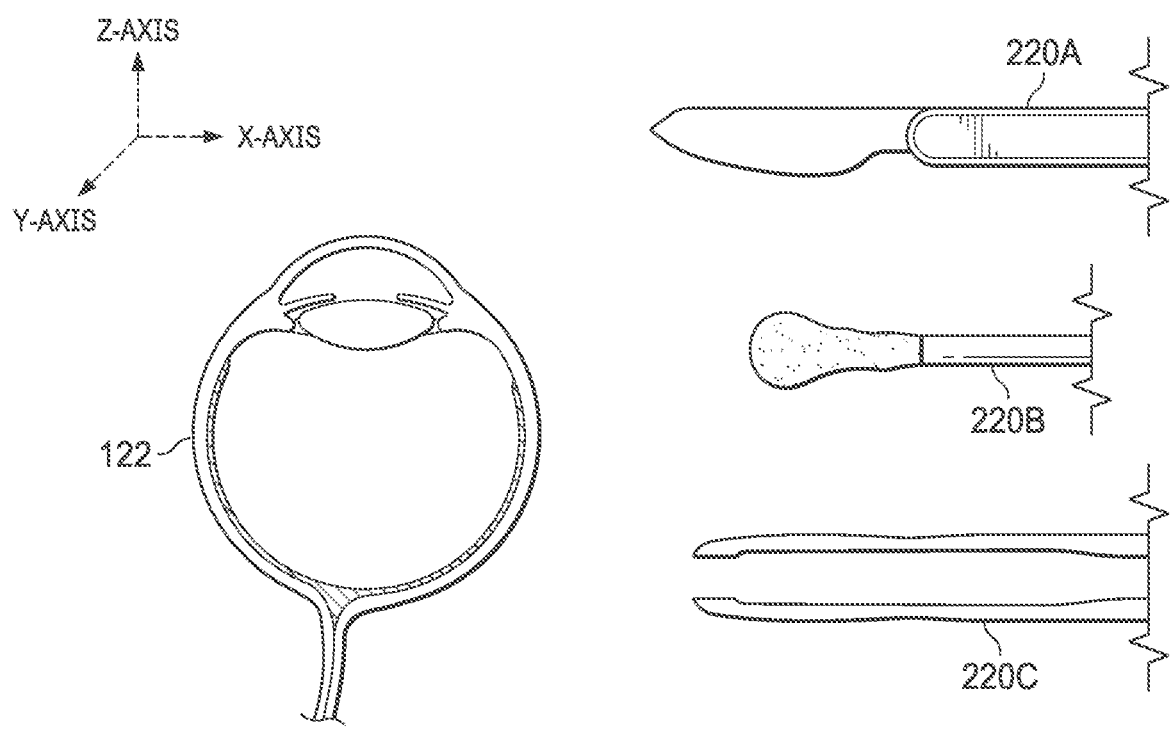

Turning now to FIG. 2C, an example of a microscope integrated display and examples of surgical tooling equipment are illustrated. As shown, surgical tooling equipment 220A may be or include a scalpel. As illustrated, surgical tooling equipment 220B may be or include a Q-tip. As shown, surgical tooling equipment 220C may be or include tweezers. Other surgical tooling equipment that is not specifically illustrated may be utilized with one or more systems, one or more processes, and/or one or more methods described herein.

As an example, surgical tooling equipment 220 may be marked with one or more patterns. The one or more patterns may be utilized in identifying surgical tooling equipment 220. The one or more patterns may include one or more of a hash pattern, a stripe pattern, and a fractal pattern, among others. As another example, surgical tooling equipment 220 may be marked with a dye and/or a paint. The dye and/or the paint may reflect one or more of visible light, infrared light, and ultraviolet light, among others. In one example, an illuminator 278 may provide ultraviolet light, and image sensor 272 may receive the ultraviolet light reflected from surgical tooling equipment 220. Computer system 230 may receive image data, based at least on the ultraviolet light reflected from surgical tooling equipment 220, from image sensor 272 and may utilize the image data, based at least on the ultraviolet light reflected from surgical tooling equipment 220, to identify surgical tooling equipment 220 from other image data provided by image sensor 272. In another example, an illuminator 278 may provide infrared light, and image sensor 272 may receive the infrared light reflected from surgical tooling equipment 220. Computer system 230 may receive image data, based at least on the infrared light reflected from surgical tooling equipment 220, from image sensor 272 and may utilize the image data, based at least on the infrared light reflected from surgical tooling equipment 220, to identify surgical tooling equipment 220 from other image data provided by image sensor 272.

As illustrated, MID 250 may include eye pieces 252A and 252B. As shown, MID 250 may include displays 262A and 262B. Surgeon 210 may look into eye pieces 252A and 252B. In one example, display 262A may display one or more images via eye piece 252A. A left eye of surgeon 210 may utilize eye piece 252A. In another example, display 262B may display one or more images via eye piece 252B. A right eye of surgeon 210 may utilize eye piece 252B. Although MID 250 is shown with multiple displays, MID 250 may include a single display 262. For example, the single display 262 may display one or more images via one or more of eye pieces 252A and 252B. MID 250 may be implemented with one or more displays 262.

As shown, MID 250 may include image sensors 272A and 272B. In one example, image sensors 272A and 272B may acquire images. In a second example, image sensors 272A and 272B may include cameras. In another example, an image sensor 272 may acquire images via one or more of visible light, infrared light, and ultraviolet light, among others. One or more image sensors 272A and 272B may provide data of images to computer system 230. Although MID 250 is shown with multiple image sensors, MID 250 may include a single image sensor 272. MID 250 may be implemented with one or more image sensors 272.

As illustrated, MID 250 may include distance sensors 274A and 274. For example, a distance sensor 274 may determine a distance to surgical tooling equipment 220. Distance sensor 274 may determine a distance associated with a Z-axis. Although MID 250 is shown with multiple image sensors, MID 250 may include a single distance sensor 274. In one example, MID 250 may be implemented with one or more distance sensors 274. In another example, MID 250 may be implemented with no distance sensor.

As shown, MID 250 may include lenses 276A and 276B. Although MID 250 is shown with multiple lenses 276A and 276B, MID 250 may include a single lens 276. MID 250 may be implemented with one or more lenses 276. As illustrated, MID 250 may include illuminators 278A and 278B. For example, an illuminator 278 may provide and/or produce one or more of visible light, infrared light, and ultraviolet light, among others. Although MID 250 is shown with multiple illuminators, MID 250 may include a single illuminator 278. MID 250 may be implemented with one or more illuminators 278. MID 250 may include one or more structures and/or one or more functionalities as those described with reference to biometry device 114. In one example, MID 250 may include OLCR device 166. In another example, MID 250 may include wavefront device 168.

Figure 3A:
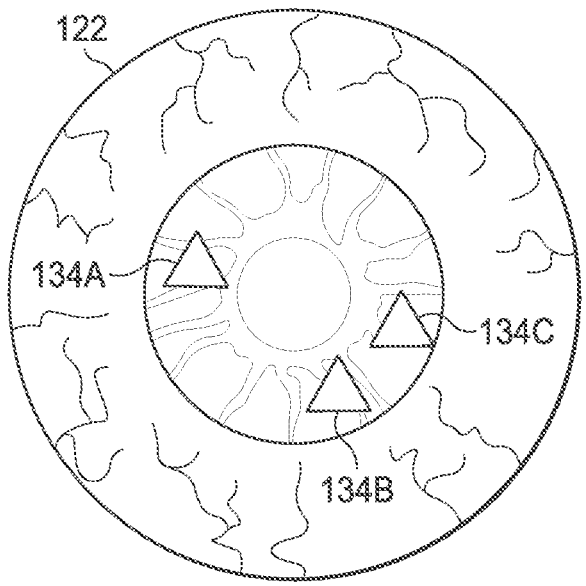
FIGS. 3A-3D illustrate examples of an eye.

Turning now to FIGS. 3A-3D, examples of an eye are illustrated. As shown in FIG. 3A, eye 122 may be oriented upwards. In one example, eye 122 may be oriented upwards without being angled. In another example, eye 122 may be oriented upwards without being rotated. Two or more of iris structures 134A-134C may be utilized in determining that eye 122 is oriented upwards. For example, computer system 230 may determine respective positions of the two or more of iris structures 134A-134C. Computer system 230 may determine that eye 122 is oriented upwards based at least one the respective positions of the two or more of iris structures 134A-134C.

Figure 3B:
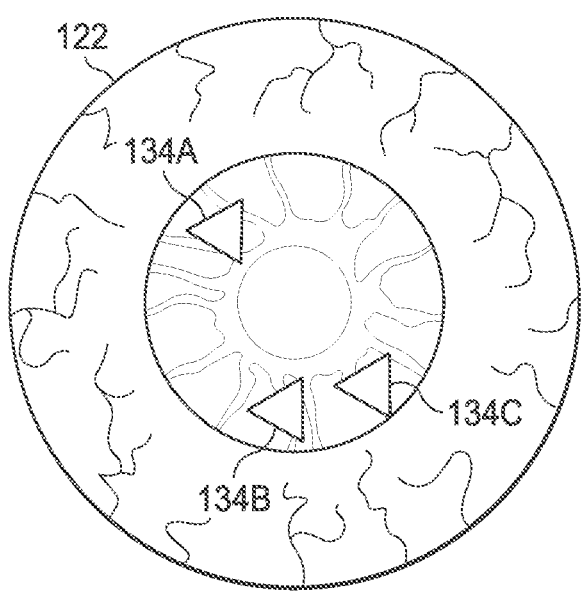

As illustrated in FIG. 3B, eye 122 may be rotated. Two or more of iris structures 134A-134C may be utilized in determining that eye 122 is rotated. For example, computer system 230 may determine respective positions of the two or more of iris structures 134A-134C. Computer system 230 may determine that eye 122 is rotated by an angle based at least one the respective positions of the two or more of iris structures 134A-134C.

Figure 3C:
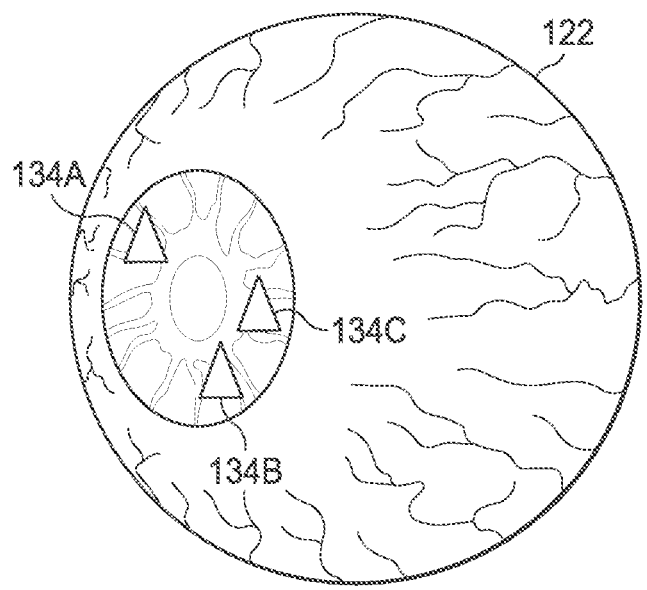

As shown in FIG. 3C, eye 122 may be angled. As illustrated, eye 122 may be angled to the left. Two or more of iris structures 134A-134C may be utilized in determining that eye 122 is angled. For example, computer system 230 may determine respective positions of the two or more of iris structures 134A-134C. Computer system 230 may determine that eye 122 is angled by an angle based at least one the respective positions of the two or more of iris structures 134A-134C.

Figure 3D:
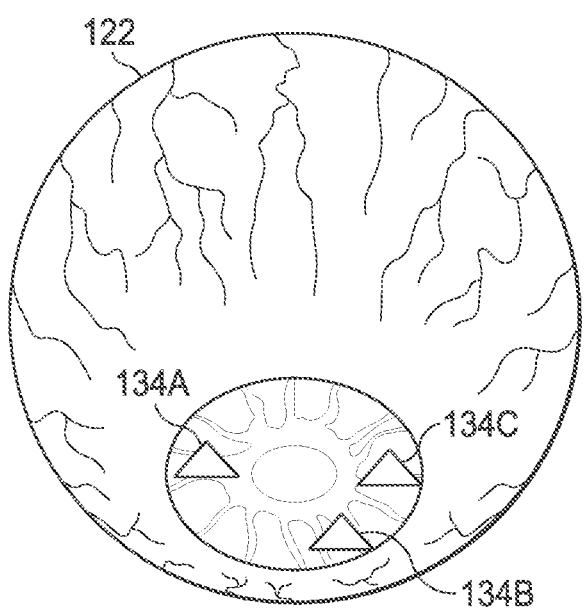

As illustrated in FIG. 3D, eye 122 may be angled. As shown, eye 122 may be angled down. Two or more of iris structures 134A-134C may be utilized in determining that eye 122 is angled. For example, computer system 230 may determine respective positions of the two or more of iris structures 134A-134C. Computer system 230 may determine that eye 122 is angled by an angle based at least one the respective positions of the two or more of iris structures 134A-134C.

Figure 3E:
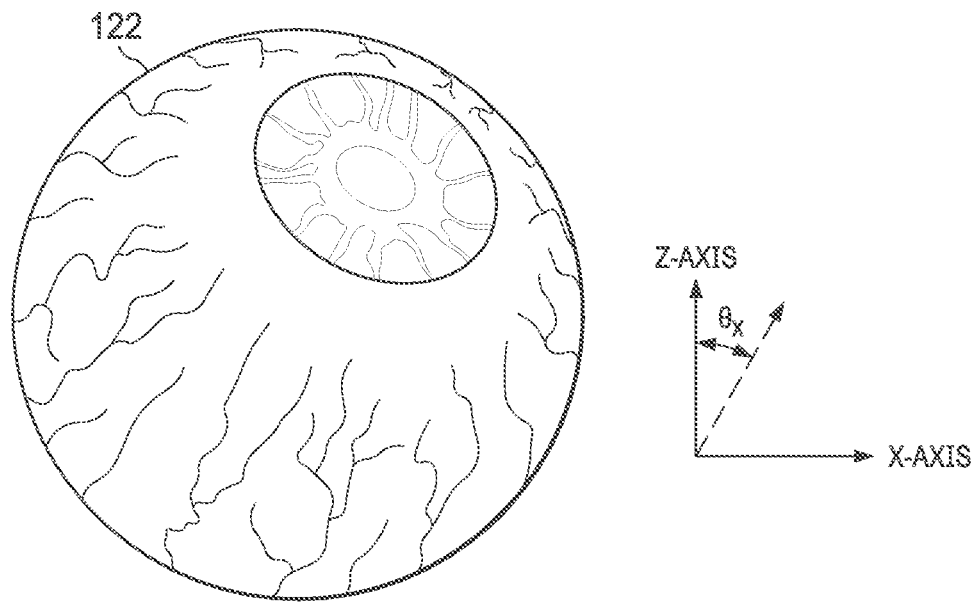
FIGS. 3E-3H illustrate examples of an eye and a coordinate system.
Figure 3F:
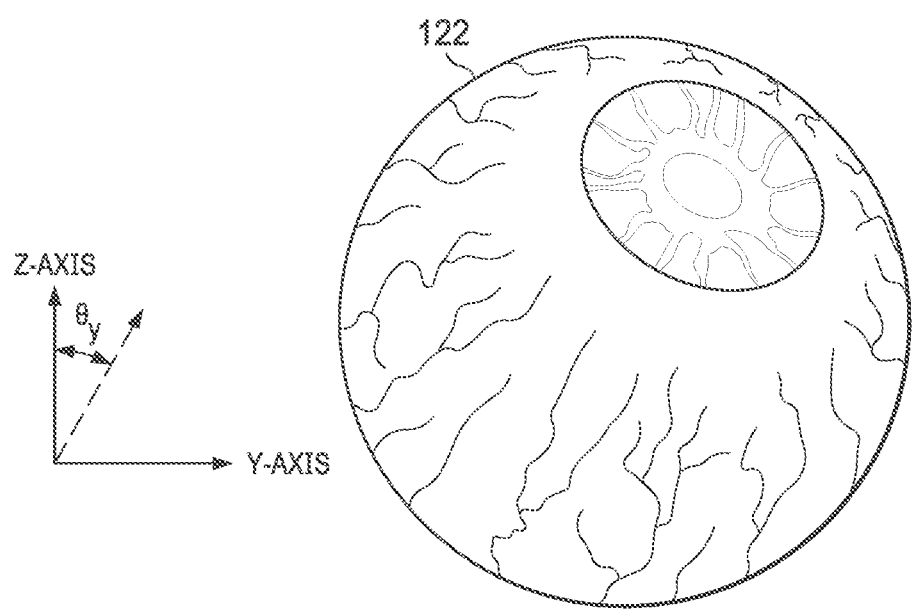
Figure 3G:
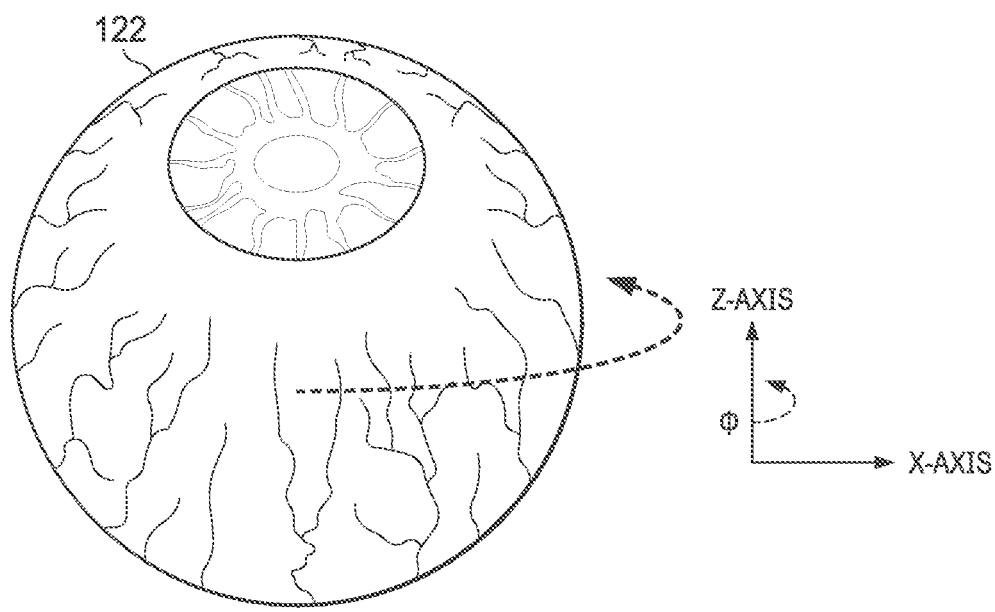
Figure 3H:
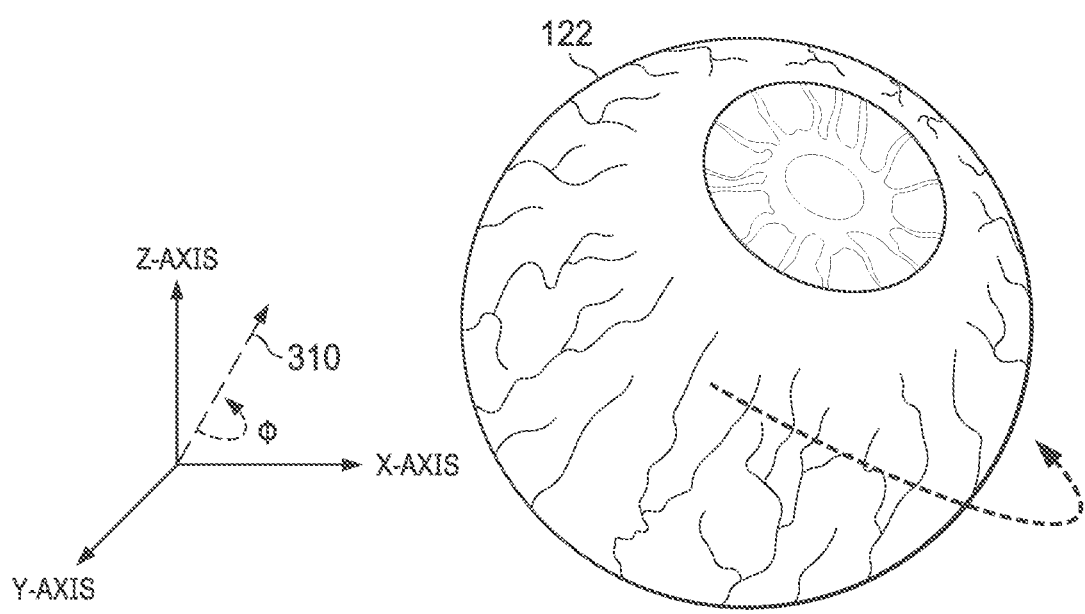

Turning now to FIGS. 3E-3H, examples of an eye and a coordinate system is illustrated. As shown in FIG. 3E, eye 122 may be at an angle $\theta_x$ from a Z-axis with respect to a X-axis. Angle $\theta_x$ may be positive or negative. As illustrated in FIG. 3F, eye 122 may be at an angle $\theta_y$ from the Z-axis with respect to a Y-axis. Angle $\theta_y$ may be positive or negative. As shown in FIG. 3G, eye 122 may be rotated by an angle $\phi$. For example, eye 122 may be rotated by angle $\phi$ about the Z-axis. Angle $\phi$ may be positive or negative. As illustrated in FIG. 3G, eye 122 may be rotated by angle $\phi$ about an arbitrary axis 310. Angle $\phi$ may be positive or negative. In one example, axis 310 may be based at least on angle $\theta_x$. In a second example, axis 310 may be based at least on angle $\theta_y$. In another example, axis 310 may be based at least on angle $\theta_x$ and based at least on angle $\theta_y$. Although FIGS. 3E-3H utilize a Cartesian coordinate system, any coordinate system may be utilized.

Figure 4A:
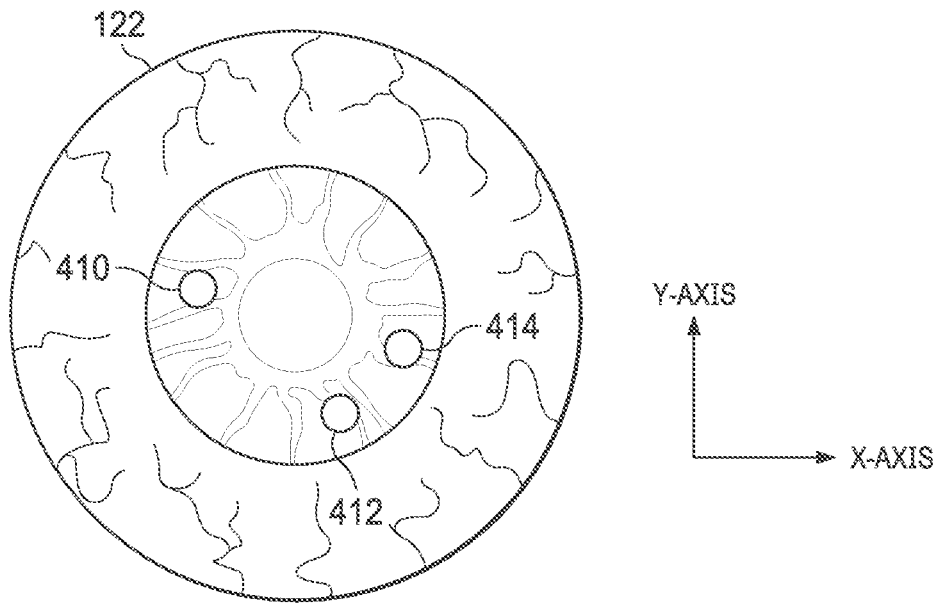
FIGS. 4A-4D illustrate examples of locations of iris structures.

Turning now to FIGS. 4A-4D, examples of locations of iris structures are illustrated. As shown in FIGS. 4A-4D, a X-axis and a Y-axis may be in a plane as illustrated. A Z-axis is not specifically illustrated. The Z-axis may be perpendicular to the X-axis and the Y-axis. The Z-axis may come from the page. Iris structures 134A-134C, as shown in FIG. 3A, may be respectively associated with positions 410-414, as illustrated in FIG. 4A. For example, iris structures 134A-134C may be respectively at positions 410-414. A position of an iris structure of iris structures 410-444 may be associated with a X-coordinate, a Y-coordinate, and a Z-coordinate.

Figure 4B:
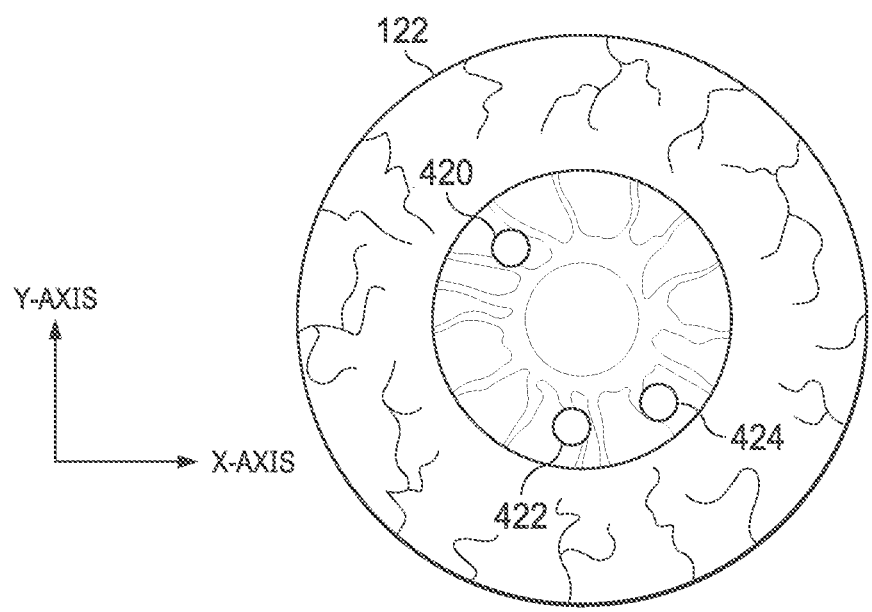
Figure 4C:
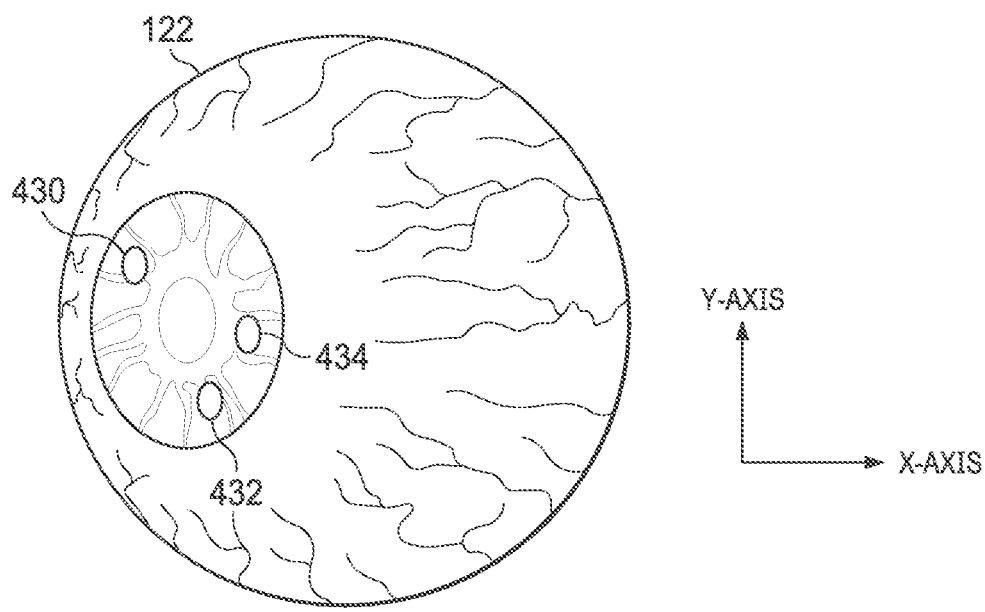
Figure 4D:
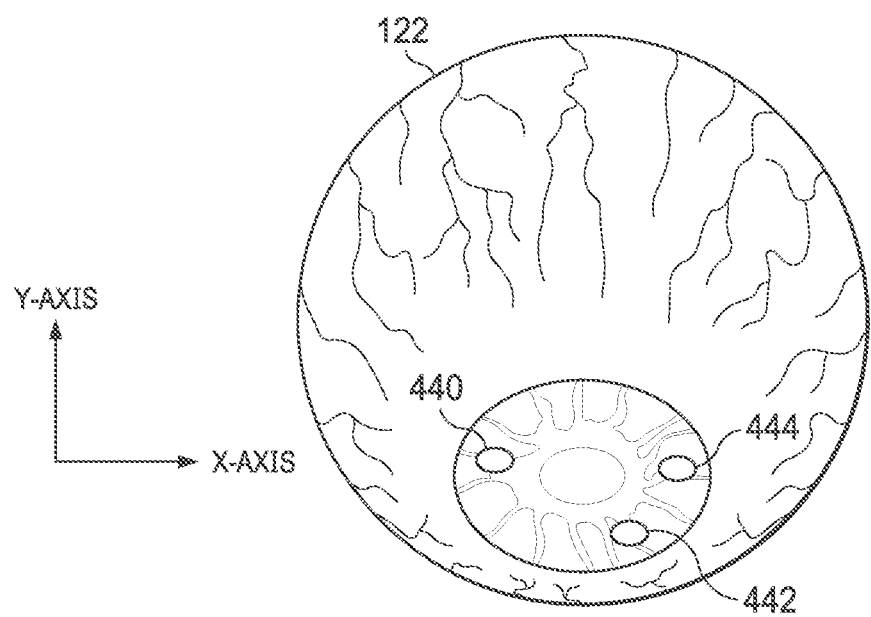

Iris structures 134A-134C, as shown in FIG. 3B, may be respectively associated with positions 420-424, as illustrated in FIG. 4B. For example, iris structures 134A-134C may be respectively at positions 420-424. Iris structures 134A-134C, as shown in FIG. 3C, may be respectively associated with positions 430-434, as illustrated in FIG. 4C. For example, iris structures 134A-134C may be respectively at positions 430-434. Iris structures 134A-134C, as shown in FIG. 3D, may be respectively associated with positions 440-444, as illustrated in FIG. 4D. For example, iris structures 134A-134C may be respectively at positions 440-444.

Figure 5A:
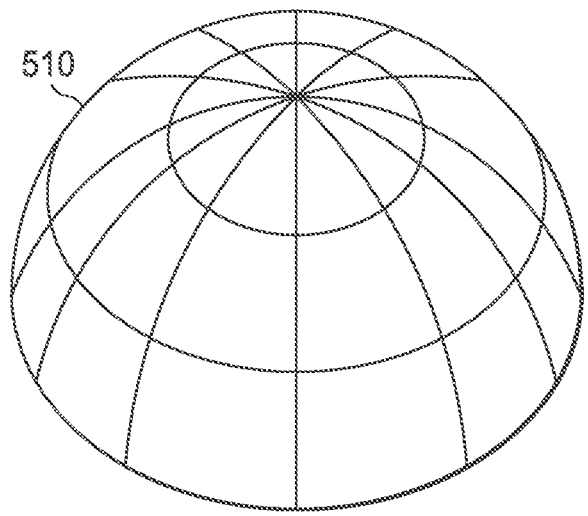
FIG. 5A illustrates an example of a wireframe overlay.

Turning now to FIG. 5A, an example of a wireframe overlay is illustrated. A three-dimensional image may be or include a wireframe overlay 510.

Figure 5B:
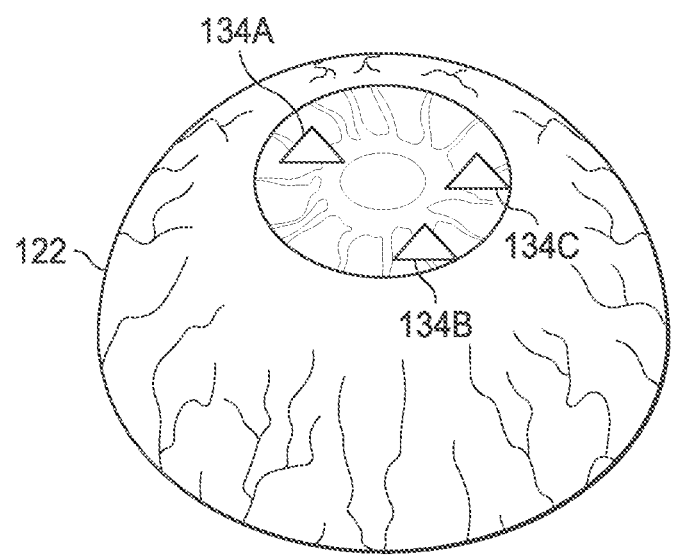
FIG. 5B illustrates an example of an eye and iris structures.

Turning now to FIG. 5B, an example of an eye and iris structures is illustrated. As shown, eye 122 may include iris structures 134A-134C.

Figure 5C:
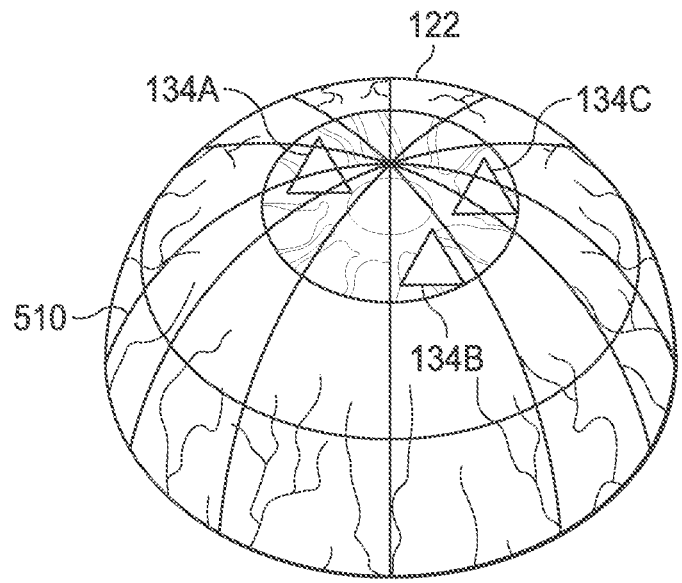
FIGS. 5C and 5D illustrate examples of three-dimensional overlays.
Figure 5D:
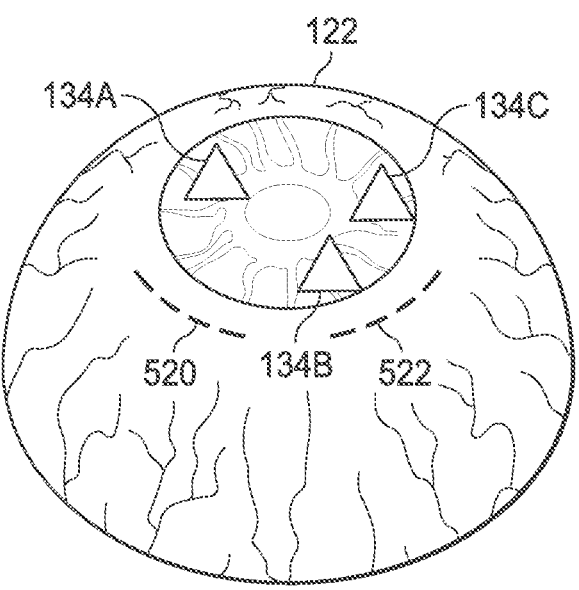

Turning now to FIGS. 5C and 5D, examples of three-dimensional images are illustrated. As shown in FIG. 5C, wireframe 510 may be displayed on a view eye 122. For example, wireframe 510 may be overlaid on a view eye 122. MID 250 may overlay wireframe 510 on a view eye 122. As illustrated in FIG. 5D, graphics 520 and 522 may be displayed on a view eye 122. For example, graphics 520 and 522 may be overlaid on a view eye 122. MID 250 may overlay graphics 520 and 522 on a view eye 122. For example, graphics 520 and 522 may indicate locations of incision sites of eye 122.

MID 250 may provide one or more three-dimensional images to surgeon 210. MID 250 may provide the one or more three-dimensional images to surgeon 210 via displays 262A and 262B. For example, the one or more three-dimensional images may include one or more three-dimensional overlay images. MID 250 may simulate one or more appearances of depth in providing the one or more three-dimensional images. Surgeon 210 may perceive one or more images as three-dimensional. For example, display 262A may provide a first two-dimensional overlay image to surgeon 210, and display 262B may concurrently provide a second two-dimensional overlay image to surgeon 210. The second two-dimensional overlay image may be slightly different from the first two-dimensional overlay image. For example, a difference of the second two-dimensional overlay image from the first two-dimensional overlay image may be in a relative horizontal position of an object in the second two-dimensional overlay image and the first two-dimensional overlay image. A positional difference of the object in the first two-dimensional overlay image and the object in the second two-dimensional overlay image may be referred to as a horizontal disparity. More generally, for example, the positional difference of the object in the first two-dimensional overlay image and the object in the second two-dimensional overlay image may be referred to as a binocular disparity.

Displays 262A and 262B may provide an illusion of depth from "flat" images (e.g., two-dimensional images) that differ in horizontal disparity. For example, display 262A may provide the first two-dimensional overlay image to a left eye of surgeon 210, and display 262B may provide the second two-dimensional overlay image to a right eye of surgeon 210. When surgeon 210 views the first two-dimensional overlay image to the left eye and concurrently views the second two-dimensional overlay image to the right eye, surgeon 210 may see a single three-dimensional overlay image. For example, a brain of surgeon 210 may accept a small horizontal disparity between the first two-dimensional overlay image to the left eye of surgeon 210 and the second two-dimensional overlay image to the right eye of surgeon 210, which may permit surgeon 210 to see (e.g., perceive) a single image with depth. This may be referred to as stereoscopy. The single image with depth may be a three-dimensional overlay image.

A stereo image may be produced via creating the first two-dimensional overlay image and the second two-dimensional overlay image. For example, the first two-dimensional overlay image may be a flat first image, and the second two-dimensional overlay image may be a flat second image. The first flat first image and the second flat image may be referred to as a stereo pair. For example, the first flat first image may be for a left eye, and the second flat first image may be for a right eye. The first flat image may be rendered with respect to a position of the left eye. The second flat image may be rendered via applying a horizontal offset to the position of the left eye. For example, the horizontal offset may be an interocular distance. A typical interocular distance, for example, may be around 6.5 cm.

MID 250 may determine an interocular distance. For example, eye pieces 252A and 252B may be adjustable. Eye pieces 252A and 252B may be adjusted for an interocular distance associated with surgeon 210. A sensor of MID 250 may be utilized in determining a distance between eye pieces 252A and 252B. For example, an interocular distance associated with surgeon 210 may be determined based at least on the distance between eye pieces 252A and 252B.

Figure 6:
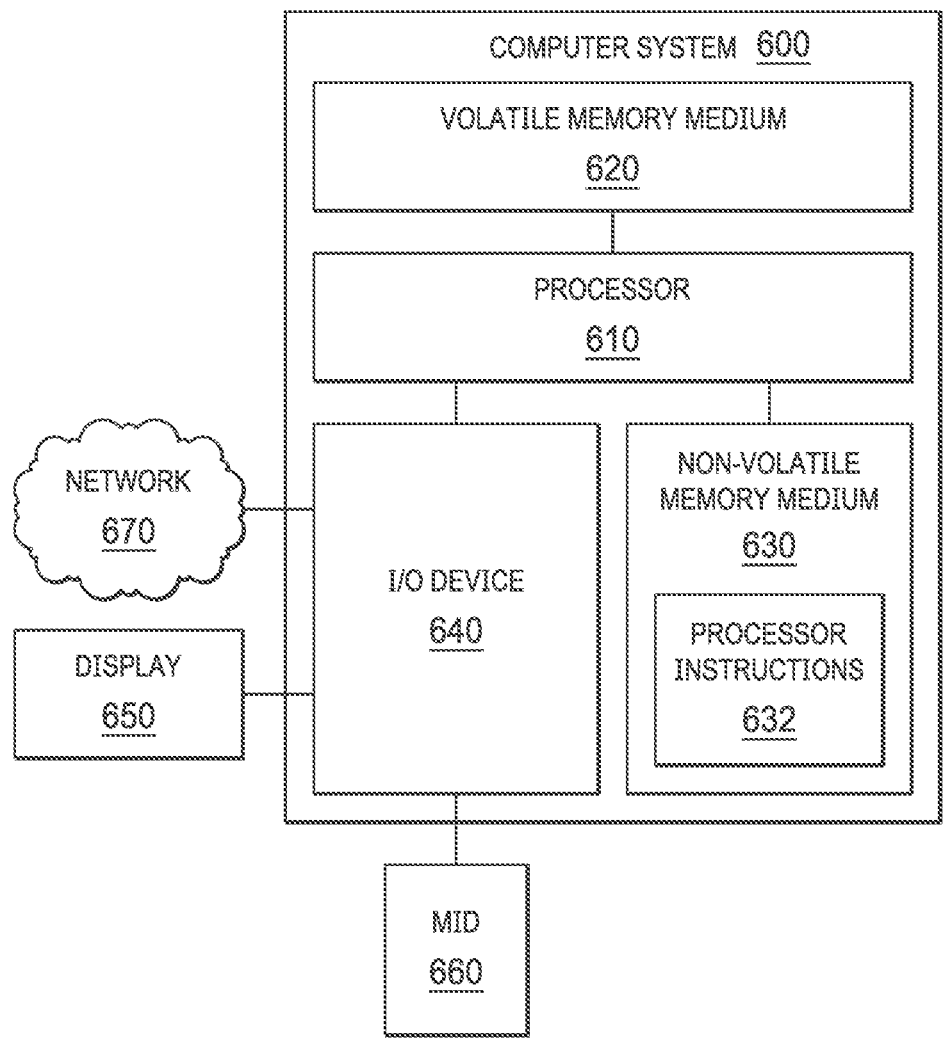
FIG. 6 illustrates an example of a computer system.

Turning now to FIG. 6, an example of a computer system is illustrated. As shown, a computer system 600 may include a processor 610, a volatile memory medium 620, a non-volatile memory medium 630, and an input/output (I/O) device 640. As illustrated, volatile memory medium 620, non-volatile memory medium 630, and I/O device 640 may be communicatively coupled to processor 610.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, non-volatile memory medium 630 may include processor instructions 632. Processor instructions 632 may be executed by processor 610. In one example, one or more portions of processor instructions 632 may be executed via non-volatile memory medium 630. In another example, one or more portions of processor instructions 632 may be executed via volatile memory medium 620. One or more portions of processor instructions 632 may be transferred to volatile memory medium 620.

Processor 610 may execute processor instructions 632 in implementing at least a portion of one or more systems, one or more flow charts, one or more processes, and/or one or more methods described herein. For example, processor instructions 632 may be configured, coded, and/or encoded with instructions in accordance with at least a portion of one or more systems, one or more flowcharts, one or more methods, and/or one or more processes described herein. Although processor 610 is illustrated as a single processor, processor 610 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 610 may include any suitable system, device, or apparatus operable to interpret and execute program instructions, process data, or both stored in a memory medium and/or received via a network. Processor 610 further may include one or more microprocessors, microcontrollers, digital signal processors (DSPs), application specific integrated circuits (ASICs), or other circuitry configured to interpret and execute program instructions, process data, or both.

I/O device 640 may include any instrumentality or instrumentalities, which allow, permit, and/or enable a user to interact with computer system 600 and its associated components by facilitating input from a user and output to a user. Facilitating input from a user may allow the user to manipulate and/or control computer system 600, and facilitating output to a user may allow computer system 600 to indicate effects of the user's manipulation and/or control. For example, I/O device 640 may allow a user to input data, instructions, or both into computer system 600, and otherwise manipulate and/or control computer system 600 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 640 may include one or more busses, one or more serial devices, and/or one or more network interfaces, among others, that may facilitate and/or permit processor 610 to implement at least a portions of one or more systems, processes, and/or methods described herein. In one example, I/O device 640 may include a storage interface that may facilitate and/or permit processor 610 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 640 may include a network interface that may facilitate and/or permit processor 610 to communicate with a network. I/O device 640 may include one or more of a wireless network interface and a wired network interface. In a third example, I/O device 640 may include one or more of a peripheral component interconnect (PCI) interface, a PCI Express (PCIe) interface, a serial peripheral interconnect (SPI) interface, and an inter-integrated circuit (I²C) interface, among others. In a fourth example, I/O device 640 may include circuitry that may permit processor 610 to communicate data with one or more sensors. In a fifth example, I/O device 640 may facilitate and/or permit processor 610 to communicate data with one or more of a display 650 and a MID 660, among others. In another example, I/O device 640 may facilitate and/or permit processor 610 to communicate data with an imaging device 670. As illustrated, I/O device 640 may be coupled to a network 680. For example, I/O device 640 may include a network interface.

Network 680 may include a wired network, a wireless network, an optical network, or a combination of the foregoing, among others. Network 680 may include and/or be coupled to various types of communications networks. For example, network 680 may include and/or be coupled to a local area network (LAN), a wide area network (WAN), an Internet, a public switched telephone network (PSTN), a cellular telephone network, a satellite telephone network, or a combination of the foregoing, among others. A WAN may include a private WAN, a corporate WAN, a public WAN, or a combination of the foregoing, among others.

A computer system described herein may include one or more structures and/or one or more functionalities as those described with reference to computer system 600. In one example, computer system 112 may include one or more structures and/or one or more functionalities as those described with reference to computer system 600. In a second example, computer system 230 may include one or more structures and/or one or more functionalities as those described with reference to computer system 600. In another example, a computer system of MID 250 may include one or more structures and/or one or more functionalities as those described with reference to computer system 600.

Figure 7:
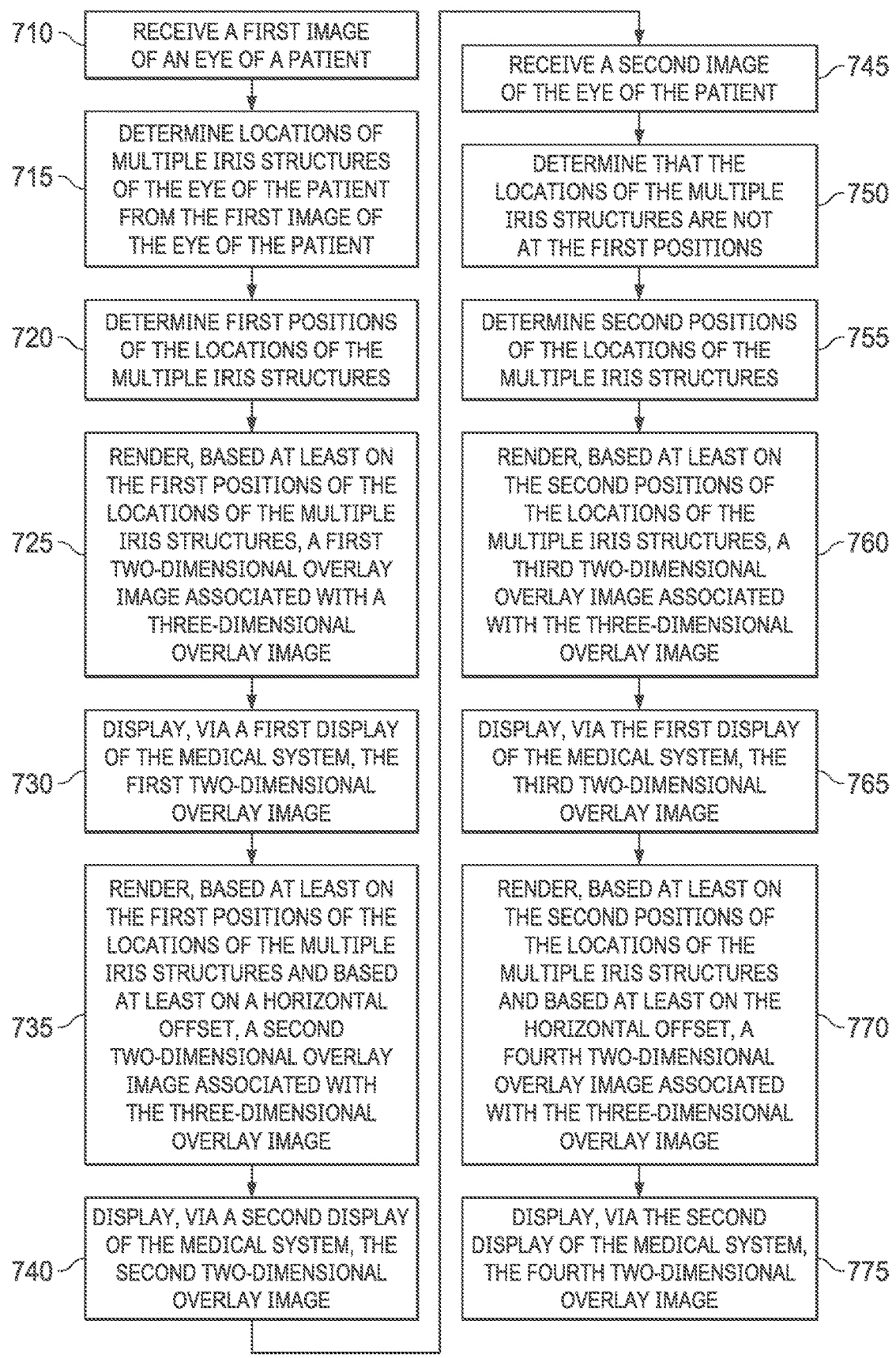
FIG. 7 illustrates an example of a method of operating a medical system.

Turning now to FIG. 7, an example of a method of operating a medical system is illustrated. At 710, a first image of an eye of a patient may be received. For example, computer system 230 may receive a first image of eye 122 of patient 120. Computer system 230 may receive the first image from an image sensor. For example, the image sensor may be or include a camera. The camera may transform light into first digital data that includes the first image of eye 122 of patient 120. For example, the camera may provide the first digital data to computer system 230. Computer system 230 may receive the first digital data.

At 715, locations of multiple iris structures of the eye of the patient from the first image of the eye of the patient may be determined. For example, locations of multiple of iris structures 134A-134C of eye 122 of patient 120 may be determined. At 720, first positions of the locations of the multiple iris structures may be determined. For example, the multiple of iris structures 134A-134C may be at first positions 410-414, as illustrated in FIG. 4A.

Determining the first positions of the locations of the multiple of iris structures 134A-134C may include determining one or more of $\theta_x$, $\theta_y$, and $\phi$. For example, $\theta_x$, $\theta_y$, and $\phi$, associated with the first positions, may be respectively associated with a first angle, a second angle, and a third angle. The first angle may be associated with a X-axis. The second angle may be associated with a Y-axis. The third angle may be associated with a Z-axis or arbitrary axis 310. In one example, if the first angle is associated with a non-zero angle or the second angle is associated with a non-zero angle, the third angle may be associated with a rotation about arbitrary axis 310. In another example, if the first angle is zero and the second angle is zero, the third angle may be associated with a rotation about the Z-axis.

Figure 8A:
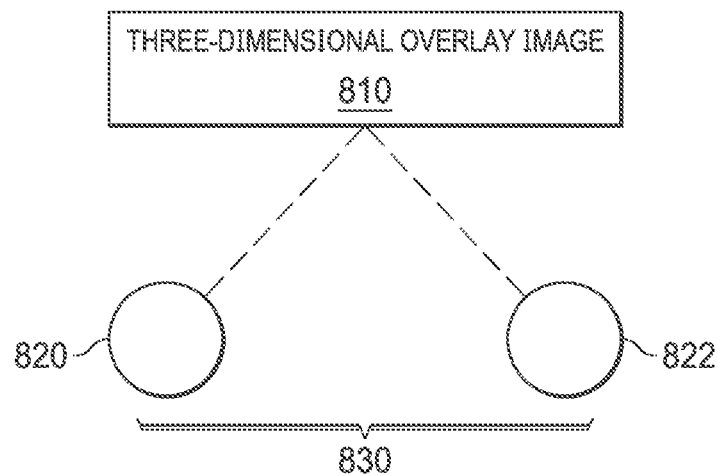
FIG. 8A illustrates an example of a three-dimensional overlay image and a horizontal offset.
Figure 8B:
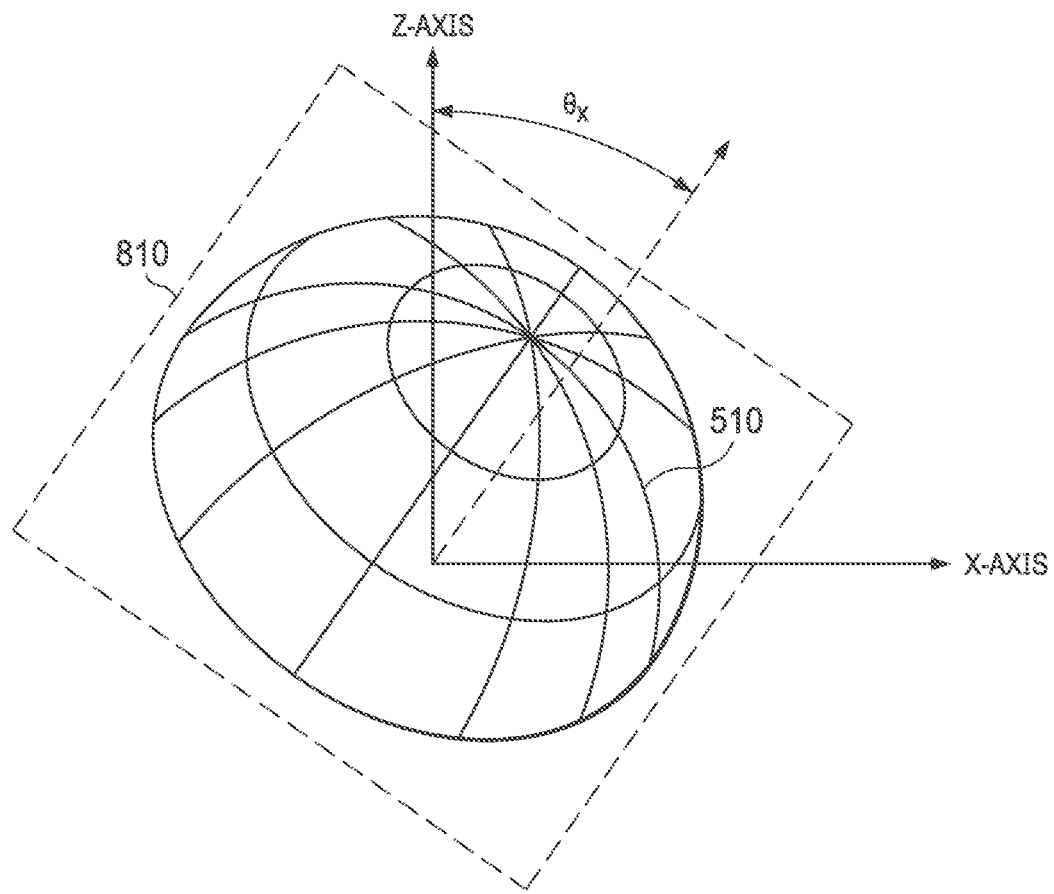
FIG. 8B illustrates an example of a three-dimensional overlay image that includes a wireframe.
Figure 8C:
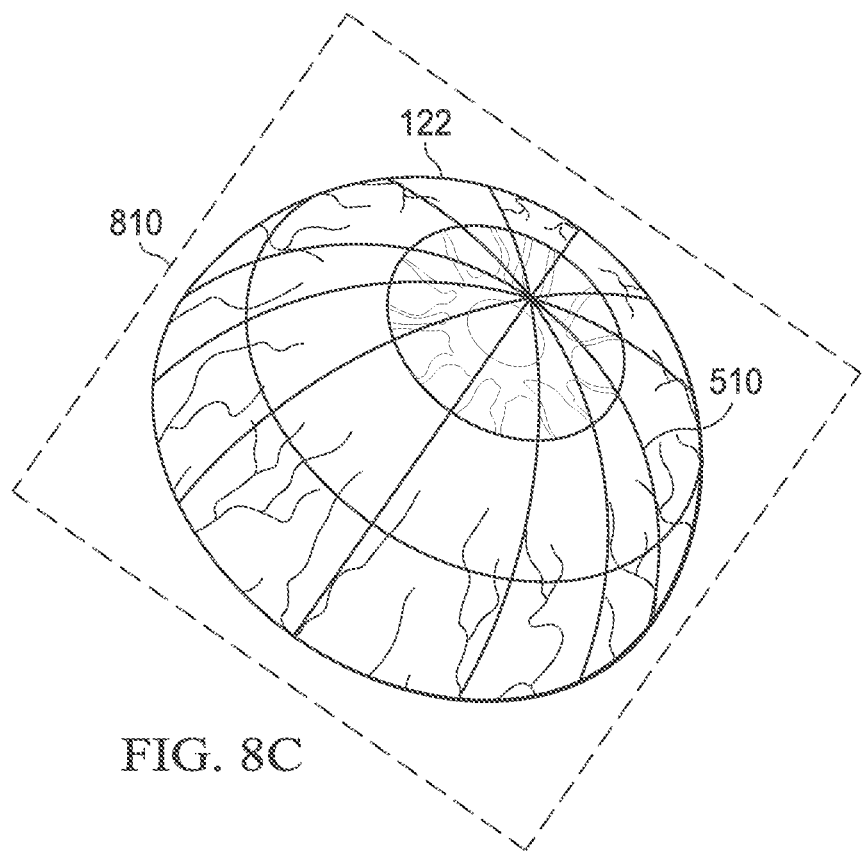
FIG. 8C illustrates an example of a three-dimensional two-dimensional overlay, rendered based at least on an angle, overlaid on an eye of a patient.
Figure 8D:
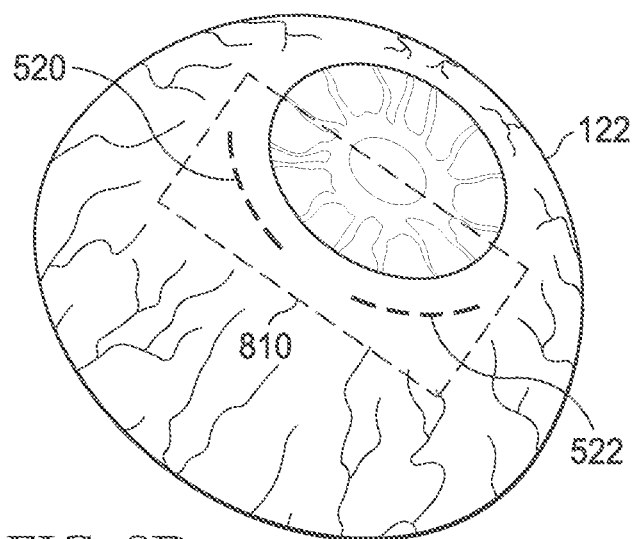
FIG. 8D illustrates an example of a three-dimensional overlay that includes graphics.

At 725, a first two-dimensional overlay image associated with a three-dimensional overlay image may be rendered based at least on the first positions of the locations of the multiple iris structures. For example, the first two-dimensional overlay image associated with the three-dimensional overlay image may be rendered based at least on a first angle associated with a X-axis, a second angle associated with a Y-axis, and an angle of rotation about an arbitrary axis. As illustrated in FIG. 8A, a first two-dimensional overlay image associated with a three-dimensional overlay image 810 may be rendered based at least on a position 820. As shown in FIG. 8B, three-dimensional overlay image 810 may include wireframe 510. For example, wireframe 510 may be rendered based at least on $\theta_x$. Wireframe 510 may be rotated by $\theta_x$. As illustrated in FIG. 8D, three-dimensional overlay image 810 may include graphics 520 and 522. For example, graphics 520 and 522 may be rendered based at least on $\theta_x$. Graphics 520 and 522 may be rotated by $\theta_x$. At 730, the first two-dimensional overlay image may be displayed via a first display of the medical system. For example, the first two-dimensional overlay image may be displayed via display 162A. Display 162A may display the first two-dimensional overlay image via eye piece 152A.

At 735, a second two-dimensional overlay image associated with the three-dimensional overlay image may be rendered based at least on the first positions of the locations of the multiple iris structures and based at least on a horizontal offset. For example, the second two-dimensional overlay image associated with the three-dimensional overlay image may be rendered based at least on the first angle associated with the X-axis, the second angle associated with the Y-axis, and the angle of rotation about the arbitrary axis and based at least on the horizontal offset. A second two-dimensional overlay image associated with three-dimensional overlay image 810 may be rendered based at least on a position 822, as illustrated in FIG. 8A. For example, the second two-dimensional overlay image associated with three-dimensional overlay image 810 may be rendered based at least on a horizontal offset 830, as shown in FIG. 8A. Horizontal offset 830 may be an interocular distance. For example, the interocular distance may be associated with a distance between eyes of surgeon 210. Horizontal offset 830 may be based at least on a distance between eye pieces 252A and 252B.

At 740, the second two-dimensional overlay image may be displayed via a second display of the medical system. For example, the second two-dimensional overlay image may be displayed via display 162B. Display 162B may display the second two-dimensional overlay image via eye piece 152B. The second two-dimensional overlay image may be displayed concurrently with the first two-dimensional overlay image. For example, when surgeon 210 views the second two-dimensional overlay image concurrently with the first two-dimensional overlay image, the second two-dimensional overlay image and the first two-dimensional overlay image may provide three-dimensional overlay image 810 to surgeon 210. Surgeon 210 may see, via MID 250, three-dimensional overlay image 810, rendered based at least on $\theta_x$, overlaid on eye 122 as illustrated in FIG. 8C. Although the examples shown in FIGS. 8B-8D illustrate a rendering based on $\theta_x$, a rendering of three-dimensional overlay image 810 may be based at least on one or more of $\theta_x$, $\theta_y$, and $\phi$.

At 745, a second image of the eye of the patient may be received. For example, computer system 230 may receive a second image of eye 122 of patient 120. Computer system 230 may receive the second image from an image sensor. For example, the image sensor may be or include a camera. The camera may transform light into second digital data. For example, the camera may provide the second digital data to computer system 230. At 750, it may be determined that the locations of the multiple iris structures are not at the first positions. For example, eye 122 may have moved. If eye 122 moved, the locations of the multiple of iris structures 134A-134C may not be at the first positions. For example, if eye 122 moved, the locations of the multiple of iris structures 134A-134C may not be at the first positions, as illustrated in FIG. 4A.

At 755, second positions of the locations of the multiple iris structures may be determined. In one example, the multiple of iris structures 134A-134C may be at second positions 420-424, as illustrated in FIG. 4B. In a second example, the multiple of iris structures 134A-134C may be at second positions 430-434, as illustrated in FIG. 4C. In another example, the multiple of iris structures 134A-134C may be at second positions 440-444, as illustrated in FIG. 4D. The second positions of the locations of the multiple iris structures may be determined in response to determining that the locations of the multiple iris structures are not at the first positions. Determining the second positions of the locations of the multiple of iris structures 134A-134C may include determining one or more of $\theta'_x$, $\theta'_y$, and $\phi'$. For example, $\theta'_x$, $\theta'_y$, and $\phi'$, associated with the second positions, may be respectively associated with the first angle, the second angle, and the third angle. At least one of $\theta'_x$, $\theta'_y$, and $\phi'$ may be different from at least one of $\theta_x$, $\theta_y$, and $\phi$, respectively.

At 760, a third two-dimensional overlay image associated with the three-dimensional overlay image may be rendered based at least on the second positions of the locations of the multiple iris structures. For example, three-dimensional overlay image 810 may change based at least on second positions of the locations of the multiple of iris structures 134A-134C. The third two-dimensional overlay image associated with the three-dimensional overlay image may be rendered based at least on a fourth angle associated with a X-axis, a fifth angle associated with a Y-axis, and an angle of rotation about an arbitrary axis. As illustrated in FIG. 8A, the third two-dimensional overlay image associated with three-dimensional overlay image 810 may be rendered based at least on position 820. Wireframe 510 may be rendered based at least on $\theta'_x$. Wireframe 510 may be rotated by $\theta'_x$. Graphics 520 and 522 may be rendered based at least on $\theta'_x$. Graphics 520 and 522 may be rotated by $\theta'_x$.

At 765, the third two-dimensional overlay image may be displayed via the first display of the medical system. For example, the third two-dimensional overlay image may be displayed via display 162A. Display 162A may display the third two-dimensional overlay image via eye piece 152A. At 770, a fourth two-dimensional overlay image associated with the three-dimensional overlay image may be rendered based at least on the first positions of the locations of the multiple iris structures and based at least on the horizontal offset. For example, the fourth two-dimensional overlay image associated with the three-dimensional two-dimensional overlay image may be rendered based at least on the fourth angle associated with the X-axis, the fifth angle associated with the Y-axis, and the angle of rotation about the arbitrary axis and based at least on the horizontal offset. A fourth two-dimensional overlay image associated with three-dimensional overlay image 810 may be rendered based at least on a position 822, as illustrated in FIG. 8A. For example, the fourth two-dimensional overlay image associated with three-dimensional overlay image 810 may be rendered based at least on horizontal offset 830, as shown in FIG. 8A.

Figure 8E:
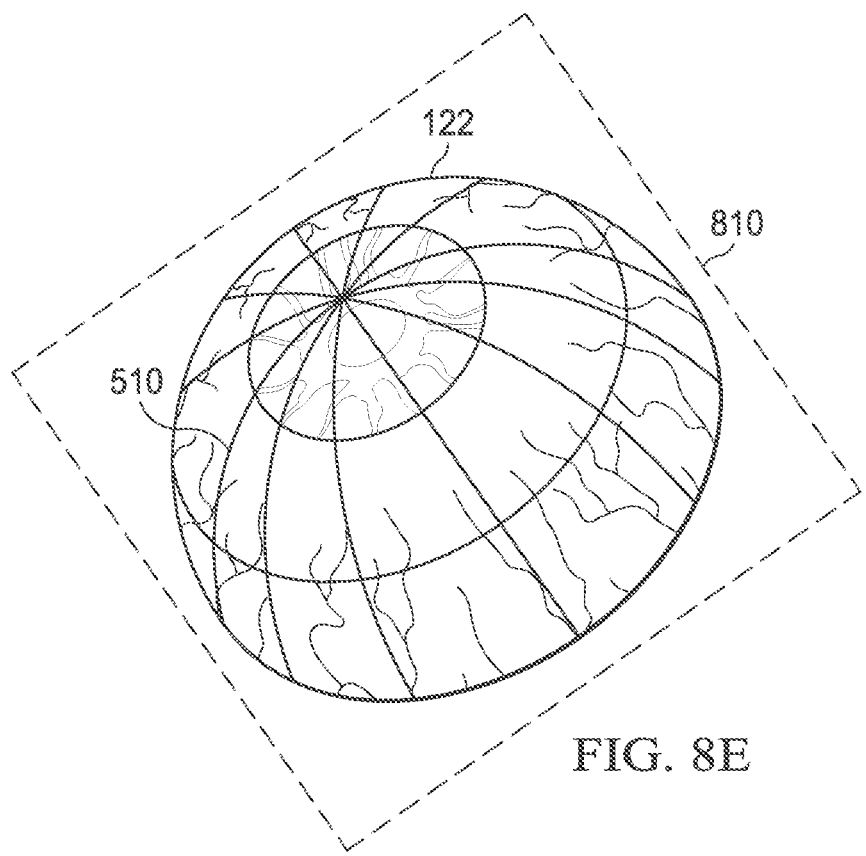
FIG. 8E illustrates another example of a three-dimensional overlay, rendered based at least on another angle, overlaid on an eye of a patient.
Figure 8F:
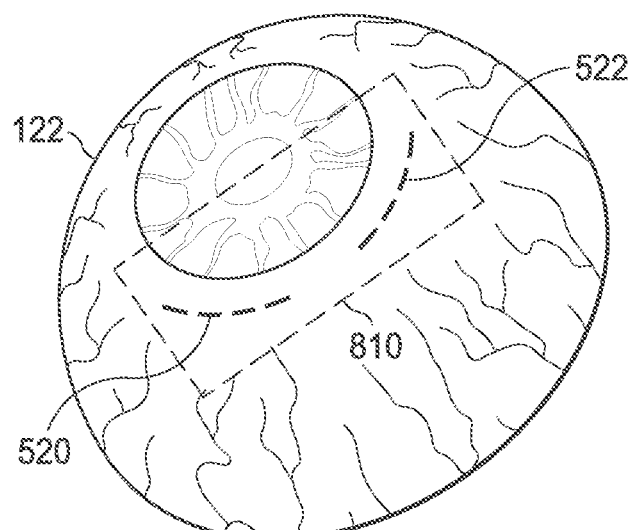
FIG. 8F illustrates another example of a three-dimensional overlay that includes graphics.

At 775, the fourth two-dimensional overlay image may be displayed via the second display of the medical system. For example, the fourth two-dimensional overlay image may be displayed via display 162B. Display 162B may display the fourth two-dimensional overlay image via eye piece 152B. The fourth two-dimensional overlay image may be displayed concurrently with the third two-dimensional overlay image. For example, when surgeon 210 views the fourth two-dimensional overlay image concurrently with the third two-dimensional overlay image, the fourth two-dimensional overlay image and the third two-dimensional overlay image may provide three-dimensional overlay image 810 to surgeon 210. Surgeon 210 may see, via MID 250, three-dimensional overlay image 810, rendered based at least on $\theta'_x$, overlaid on eye 122 as illustrated in FIG. 8E. Three-dimensional overlay image 810 may include graphics 520 and 522, as shown in FIG. 8F. For example, graphics 520 and 522 may indicate incision sites of eye 122. Although the examples shown in FIGS. 8E and 8F illustrate a rendering based on $\theta'_x$, a rendering of three-dimensional overlay image 810 may be based at least on one or more of $\theta'_x$, $\theta'_y$, and $\phi'$.

One or more of the method and/or process elements and/or one or more portions of a method and/or processor elements may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

A memory medium may be and/or may include an article of manufacture. For example, the article of manufacture may include and/or may be a software product and/or a program product. The memory medium may be coded and/or encoded with processor-executable instructions in accordance with one or more flowcharts, systems, methods, and/or processes described herein to produce the article of manufacture.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:
1. A medical system, comprising:
   at least one processor;
   a binocular digital microscope having a first ocular having a first display and a second ocular having a second display, wherein the binocular digital microscope is communicatively coupled to the processor; and
   a memory medium that is coupled to the at least one processor and that includes instructions, when executed by the at least one processor, cause the system to:
      receive a first image of an eye of a patient;

determine locations of multiple iris structures of the eye of the patient from the first image of the eye of the patient;
determine first positions of the locations of the multiple iris structures;
render, based at least on the first positions of the locations of the multiple iris structures, a first two-dimensional overlay image associated with a three-dimensional overlay image;
display, via the first display of the plurality of displays, the first two-dimensional overlay image associated with the three-dimensional overlay image;
render, based at least on the first positions of the locations of the multiple iris structures and based at least on a horizontal offset, a second two-dimensional overlay image associated with the three-dimensional overlay image, wherein the horizontal offset is an interocular distance between the first ocular and the second ocular;
display, via the second display of the plurality of displays, the second two-dimensional overlay image associated with the three-dimensional overlay image;
receive a second image of the eye of the patient;
determine second positions of the locations of the multiple iris structures from the second image of the eye of the patient;
render, based at least on the second positions of the locations of the multiple iris structures, a third two-dimensional overlay image associated with the three-dimensional overlay image;
display, via the first display, the third two-dimensional overlay image associated with the three-dimensional overlay image;
render, based at least on the second positions of the locations of the multiple iris structures and based at least on the horizontal offset, a fourth two-dimensional overlay image associated with the three-dimensional overlay image; and
display, via the second display, the fourth two-dimensional overlay image associated with the three-dimensional overlay image, wherein the display of the third two-dimensional image and the display of the fourth two-dimensional image separated by the horizontal offset create a binocular disparity and a depth perception when viewed through the first ocular and the second ocular.

2. The system of claim 1, wherein the instructions further cause the system to:
determine that the locations of the multiple iris structures are not at the first positions.

3. The system of claim 2, wherein determining the second positions of the locations of the multiple iris structures is performed in response to determining that the locations of the multiple iris structures are not at the first positions.

4. The system of claim 1, wherein the instructions further cause the system to: determine the inter-ocular distance based at least on the distance between the first ocular and the second ocular.

5. The system of claim 1, wherein the inter-ocular distance is associated with a distance between eyes of a surgeon.

6. The system of claim 1, wherein the three-dimensional overlay image includes at least one graphic that indicates an incision location associated with the eye of the patient.

7. The system of claim 1, wherein, to determine the first positions of the locations of the multiple iris structures, the instructions further cause the system to determine at least one of a first angle associated with a X-axis, a second angle associated with a Y-axis, and an angle of rotation about an arbitrary axis.

8. A method of operating a medical system, comprising:
receiving a first image of an eye of a patient;
determining locations of multiple iris structures of the eye of the patient from the first image of the eye of the patient;
determining first positions of the locations of the multiple iris structures;
rendering, based at least on the first positions of the locations of the multiple iris structures, a first two-dimensional overlay image associated with a three-dimensional overlay image;
displaying, via a first ocular of a binocular digital microscope having the first ocular having a first display and a second ocular having a second display, the first two-dimensional overlay image associated with the three-dimensional overlay image;
rendering, based at least on the first positions of the locations of the multiple iris structures and based at least on a horizontal offset, a second two-dimensional overlay image associated with the three-dimensional overlay image;
displaying, via the second ocular, the second two-dimensional overlay image associated with the three-dimensional overlay image;
receiving a second image of the eye of the patient;
determining second positions of the locations of the multiple iris structures from the second image of the eye of the patient;
rendering, based at least on the second positions of the locations of the multiple iris structures, a third two-dimensional overlay image associated with the three-dimensional overlay image;
displaying, via the first ocular, the third two-dimensional overlay image associated with the three-dimensional overlay image;
rendering, based at least on the second positions of the locations of the multiple iris structures and based at least on the horizontal offset, a fourth two-dimensional overlay image associated with the three-dimensional overlay image; and
displaying, via the second ocular, the fourth two-dimensional overlay image associated with the three-dimensional overlay image, wherein the display of the third two-dimensional image and the display of the fourth two-dimensional image separated by the horizontal offset create a binocular disparity and a depth perception when viewed through the first ocular and the second ocular.

9. The method of claim 8, further comprising:
determining that the locations of the multiple iris structures are not at the first positions.

10. The method of claim 9, wherein the determining the second positions of the locations of the multiple iris structures is performed in response to the determining that the locations of the multiple iris structures are not at the first positions.

11. The method of claim 8, wherein the horizontal offset is an interocular distance.

12. The method of claim 11, wherein the interocular distance is associated with a distance between eyes of a surgeon.

13. The method of claim 8, wherein the three-dimensional overlay image includes at least one graphic that indicates an incision location associated with the eye of the patient.

14. The method of claim 8, wherein the determining the first positions of the locations of the multiple iris structures includes determining at least one of a first angle associated with a X-axis, a second angle associated with a Y-axis, and an angle of rotation about an arbitrary axis.

* * * * *